US010384031B1

(12) United States Patent
Acker et al.

(10) Patent No.: US 10,384,031 B1
(45) Date of Patent: Aug. 20, 2019

(54) SYSTEMS AND METHODS FOR MANUFACTURING AND SAFETY OF AN $NO_2$-TO-NO REACTOR CARTRIDGE USED TO DELIVER NO FOR INHALATION THERAPY TO A PATIENT

(71) Applicant: Mallinckrodt Hospital Products IP Limited, Dublin (IE)

(72) Inventors: Jaron M. Acker, Madison, WI (US); Thomas Kohlmann, McFarland, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 970 days.

(21) Appl. No.: 14/744,298

(22) Filed: Jun. 19, 2015

Related U.S. Application Data

(60) Provisional application No. 62/015,088, filed on Jun. 20, 2014.

(51) Int. Cl.
*A61M 16/12* (2006.01)
*B01J 8/02* (2006.01)
*A61M 16/00* (2006.01)
*A61M 16/08* (2006.01)
(Continued)

(52) U.S. Cl.
CPC ...... *A61M 16/122* (2014.02); *A61M 16/0003* (2014.02); *A61M 16/0051* (2013.01); *A61M 16/0875* (2013.01); *A61M 16/20* (2013.01); *B01J 8/02* (2013.01); *G01F 1/34* (2013.01); *A61M 2016/003* (2013.01); *A61M 2202/0275* (2013.01); *A61M 2205/18* (2013.01); *A61M 2205/3334* (2013.01); *A61M 2205/35* (2013.01);
(Continued)

(58) Field of Classification Search
CPC .. A61M 2202/0275; A61M 2205/3334; A61M 2205/18; A61M 2205/35; A62D 3/30; C01B 21/32; C01B 21/24; C01B 21/203; C01B 21/28; C01B 21/26; B01J 8/02; B01J 2208/02; B01J 2208/0883
See application file for complete search history.

(56) References Cited

U.S. PATENT DOCUMENTS

| 3,106,458 A | 10/1963 | Grosskoph |
| 3,397,153 A | 8/1968 | Sippel |
| 5,558,083 A | 9/1996 | Bathe et al. |

(Continued)

OTHER PUBLICATIONS

INOmax DS (Delivery System): Operation Manual (800 ppm INOMAX (nitric oxide) for Inhalation), Ikaria, Inc. 2010, 112 pages.

(Continued)

*Primary Examiner* — Gregory A Anderson
*Assistant Examiner* — Margaret M Luarca

(57) ABSTRACT

The principles and embodiments of the present invention relate to methods and systems for safely providing NO to a recipient for inhalation therapy. There are many potential safety issues that may arise from using a reactor cartridge that converts $NO_2$ to NO, including exhaustion of consumable reactants of the cartridge reactor. Accordingly, various embodiments of the present invention provide systems and methods of determining the remaining useful life of a $NO_2$-to-NO reactor cartridge and/or a breakthrough of $NO_2$, and providing an indication of the remaining useful life and/or breakthrough.

10 Claims, 11 Drawing Sheets

(51) Int. Cl.
*A61M 16/20* (2006.01)
*G01F 1/34* (2006.01)

(52) U.S. Cl.
CPC . *A61M 2205/50* (2013.01); *B01J 2208/00893* (2013.01); *B01J 2208/02* (2013.01)

(56) References Cited

U.S. PATENT DOCUMENTS

| | | | |
|---|---|---|---|
| 5,569,151 A * | 10/1996 | Karwacki | B01J 4/00 137/264 |
| 5,732,693 A | 3/1998 | Bathe et al. | |
| 5,752,504 A | 5/1998 | Bathe | |
| 5,906,718 A | 5/1999 | Hance et al. | |
| 6,125,846 A | 10/2000 | Bathe et al. | |
| 7,523,752 B2 | 4/2009 | Montgomery et al. | |
| 8,083,997 B2 | 12/2011 | Rounbehler et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,431,163 B2 | 4/2013 | Baldassarre et al. | |
| 8,573,209 B2 | 11/2013 | Bathe et al. | |
| 8,573,210 B2 | 11/2013 | Bathe et al. | |
| 8,607,785 B2 | 12/2013 | Fine et al. | |
| 8,646,445 B2 | 2/2014 | Fine et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2006/0054018 A1 * | 3/2006 | Brestovansky | B01D 53/0407 95/95 |
| 2006/0174880 A1 * | 8/2006 | Jagger | A61M 16/10 128/201.25 |
| 2010/0104667 A1 * | 4/2010 | Fine | A61M 16/10 424/718 |
| 2012/0055815 A1 * | 3/2012 | Truex | A62B 9/006 206/205 |
| 2013/0239961 A1 * | 9/2013 | Ross, Jr. | A61M 16/10 128/202.22 |
| 2015/0367087 A1 * | 12/2015 | Dor Zidon | B01J 7/00 604/26 |

OTHER PUBLICATIONS

INOvent Delivery System: Operation and Maintenance Manual (CGA Variant), Datex-Ohmeda, Inc. 2000, 180 pages.
Using the INOpulse DS Subject Guide, Ikaria, Inc. 2012, 50 pages.
INOmax Label, Nitric Oxide Gas, INO Therapeutics 2013, 2 pages.
INOmax DSIR (Delivery System): Operation Manual (800 ppm INOMAX (nitric oxide) for Inhalation), Ikaria, Inc. 2012, 136 pages.

* cited by examiner

SYSTEMS AND METHODS FOR MANUFACTURING AND SAFETY OF AN $NO_2$-TO-NO REACTOR CARTRIDGE USED TO DELIVER NO FOR INHALATION THERAPY TO A PATIENT

CROSS-REFERENCE TO RELATED APPLICATIONS

This application claims the benefit under 35 U.S.C. § 119(e) to U.S. Provisional Application No. 62/015,088, filed Jun. 20, 2014, the entire contents of which are incorporated herein by reference in their entirety.

TECHNICAL FIELD

Principles and embodiments of the present invention relate generally to systems and methods for manufacturing of an $NO_2$-to-NO reactor cartridge for delivering NO to a patient, in need thereof, for inhalation therapy, and addressing safety aspects of such manufacturing processes.

BACKGROUND

A number of gases have been shown to have pharmaceutical action in humans and animals. One such gas is Nitric Oxide (NO) that, when inhaled, acts to dilate blood vessels in the lungs, improving oxygenation of the blood and reducing pulmonary hypertension. In the field of inhalation therapy for various pulmonary conditions such as acute pulmonary vasoconstriction, hypertension and thromboembolism, or inhalation injury, treatment has included the use of the therapeutic gas NO supplied from a gas cylinder. More specifically, this gaseous NO for inhalation therapy is supplied to a patient from a high pressure gas cylinder containing NO. For example, such an approach is disclosed in U.S. Pat. No. 5,558,083 entitled "Nitric Oxide Delivery System", which is incorporated herein by reference in its entirety.

Unlike supplying NO for inhalation therapy from a high pressure NO cylinder; some have proposed supplying NO for inhalation therapy from a source of Nitrogen Dioxide ($NO_2$), which is toxic, and converting this toxic $NO_2$ into NO using a "cartridge" or "reactor" ($NO_2$-to-NO reactor cartridge) at the patient's bedside. For example, such an approach is disclosed in U.S. Pat. No. 8,083,997 ("the '997 Patent") issued Dec. 27, 2011, to Rounbehler et al., and assigned to GENO, LLC, which is incorporated herein by reference in its entirety. The $NO_2$-to-NO reactor cartridge in the '997 Patent is filled with a loosely packed powder of a surface-active material (e.g., silica) coated with an aqueous solution of an antioxidant (e.g., aqueous ascorbic acid). Purportedly, the reactor receives $NO_2$ that passes through the loosely packed silica coated with the aqueous ascorbic acid and undergoes a chemical reaction that converts $NO_2$ to NO, which in turn exits the reactor cartridge and is then delivered to the patient.

Substantial patient safety and efficacy concerns arise from converting toxic $NO_2$ to NO at the patient's bedside as proposed because of at least the toxic nature of $NO_2$. For example, as pointed out in the '997 Patent, "unlike NO, the part per million levels of $NO_2$ gas is highly toxic if inhaled and can form nitric and nitrous acid in the lungs."

Compounding risks relating to such $NO_2$ to NO conversion at the patient's bedside, the ability of these $NO_2$-to-NO reactor cartridges to convert $NO_2$ to NO exhausts as it uses a consumable reactant and this exhaustion results in the breakthrough of toxic $NO_2$, which in turn may be delivered to the patient. Without an indicator (e.g., dosage meter) to the user of the amount of lifetime remaining for the reactor as it exhausts, a user has no way of confirming how much or little lifetime the reactor has prior to at least breakthrough of toxic $NO_2$. This can force the user to guess how much lifetime the reactor has prior to at least breakthrough of toxic $NO_2$; However, factors impacting the lifetime of the reactor and/or breakthrough of toxic $NO_2$ may not be readily ascertainable by user observation.

Further compounding risks relating to such $NO_2$-to-NO reactor cartridges, the ability of these reactors to convert $NO_2$ to NO (e.g., lifetime) can become compromised resulting in breakthrough of toxic $NO_2$ being delivered to the patient. For example, the reactor can be compromised by a channel that allows $NO_2$ flow through the reactor cartridge without conversion to NO as disclosed in U.S. Pat. No. 8,646,445 ("the '445 Patent") issued Feb. 11, 2014, to Fine et al., and assigned to GENO, LLC, which is incorporated herein by reference in its entirety. As pointed out in the '445 Patent, "Creation of a channel negates the effect of the powder and renders the cartridge useless. This problem is so severe that a packed tube like this can only be used if the cartridge is vertical."

Another $NO_2$-to-NO reactor cartridge is discussed in U.S. Pat. No. 8,607,785 ("the '785 Patent") issued Dec. 17, 2013, to Fine et al., and assigned to GENO, LLC, which is incorporated herein by reference in its entirety. Rather than a loosely packed reactor cartridge, the '785 Patent discloses a porous solid structure, which provides a rigid structure coated with an aqueous solution of an antioxidant. However, such a porous solid structure can be brittle and have its structural integrity compromised by sudden shocks or rough handling, as might occur in shipping, a clinical setting, and/or by user error, handling of the conversion reactor, and environmental factors, to name a few. For example, cracks can be formed in the structure which can provide a channel allowing flow of $NO_2$ through the reactor without conversion to NO, which in turn may be delivered to the patient. Further, cracks in the structure may not be obvious until a gas flow is applied and/or $NO_2$ breakthrough occurs. In another scenario, a crack in the porous solid structure may not initially propagate all the way through the structure until sometime later under routine usage, when a toxic $NO_2$ suddenly exits the reactor cartridge, which in turn may be delivered to the patient. Accordingly, such compromised reactors may have unforeseen shortened lifetimes.

In addition, the use of multiple containers in a medical environment holding toxic $NO_2$ presents the possibility of leaks that could release the $NO_2$ and subject both patients and staff to the toxic gas.

The above are only a few of the exemplary scenarios which can result in a patient receiving toxic $NO_2$ using the proposed techniques of converting toxic $NO_2$ to NO at the patient's bedside using an exhaustible reactor cartridge when lifetime of reactor is unknown to the user. Given the risk of serious injury or death associated with inhalation of $NO_2$ along with compounding factors and/or failure modes which may not be readily ascertainable by a user (e.g., reactor exhaustion, channeling, compromised reactors, $NO_2$ breakthrough, leaks, etc.) a need exists to provide both a reasonable assurance that the reactor cartridge is functional and a form of indication to inform a user of the amount of lifetime remaining for the reactor.

In addition, Nitrogen Dioxide, $NO_2$, reacts with water to give a mixture of nitrous and nitric acids, as shown below.

$$2NO_2 + H_2O \rightarrow HNO_2 + HNO_3$$

The presence of excess water in a reactor cartridge can provide an environment where the $NO_2$ adsorbed on the consumable conversion media can react with the water before being converted to NO. Such reactions can produce $HNO_3$ and $HNO_2$ within the reactor cartridge, which may be carried to a patient.

SUMMARY

There are several ways to address the above problems, including monitoring the use of the reactor(s), including indicators that visually warn a user of hazardous operating conditions, detectors that detect the presence or absence of the chemical species of interest, and meters that follow the depletion and/or operation of the system in real time. In addition, various steps and processes may be implemented during the manufacturing and shipping of such reactor cartridges to help insure the proper performance and functioning of the cartridge when disseminated into the field, and safety features may be incorporated into the reactor cartridge to ensure that it has been properly handled and installed.

Principles and embodiment of the present invention relate to systems and methods of preparing a $NO_2$-to-NO reactor cartridge and/or testing the safety of the cartridge before being implemented for supplying NO through inhalation therapy to a patient.

Principles and embodiments of the present invention also relate to systems and methods of assuring the safety and operability of reactor cartridges being manufactured.

Principles and embodiments of the present invention also relate to means of monitoring the manufacture and assembly of an inhalation therapy system that converts $NO_2$ to NO comprising a source of $NO_2$, a conversion reactor, and a delivery member.

Principles and embodiments of the present invention also relate to systems and methods of reducing the likelihood or preventing a significant and/or catastrophic breakthrough of $NO_2$ and preventing harmful or lethal doses of $NO_2$ from reaching the inhalation therapy recipient due to channeling and/or breakage of the consumable conversion media in a reactor cartridge.

Principles and embodiments of the present invention also relate to a system that produces a time-variable gas flow and tracks the flow and humidity entering and/or leaving the reactor cartridge to inform a user of the amount of remaining life of a reactor and provides a safety check for proper reactor preparation and operation.

Principles and embodiments of the present invention also relate to systems and methods to monitor and detect the physical treatment of reactor cartridge(s) between initial assembly and final usage to determine if a cartridge was physically abused.

Principles and embodiments of the present invention also relate to a NO gas delivery system for safely delivering a supply of NO to a recipient, comprising a gas source that supplies a gas, wherein the gas comprises one or more of $NO_2$ or NO, a gas conduit connected to and in fluid communication with the gas source, a $NO_2$-to-NO reactor cartridge connected to and in fluid communication with the gas conduit, so as to allow gas to flow from the gas source to an inlet end of the conversion reactor, a ventilator, a delivery conduit connected to and in fluid communication with an outlet end of the reactor cartridge that allows NO gas from the conversion reactor to flow to a recipient, a computer in electronic communication with the NO gas delivery system, which may include the ventilator, over a communication path, wherein the computer is configured to receive electronic signals from the reactor cartridge, a flow meter, and/or ventilator and calculate a usage level for comparison with a predetermined threshold value, and configured to generate an actuating signal when the usage level falls below the threshold value, a regulating means in electronic communication with the computer over a communication path, wherein the regulating means is configured to receive an actuating signal from the computer, and wherein the regulating means halts the delivery of the gas to a recipient.

In addition, embodiments of the present invention relate to a reactor cartridge comprising an integrated $NO_2$ sensor for measuring the amount of $NO_2$ gas exiting the $NO_2$-to-NO reactor cartridge, a flow meter for measuring the amount of $NO_2$ gas entering the reactor cartridge and/or gas being delivered to the recipient, an $NO_2$ sensor operationally associated with the delivery conduit to determine the presence of an unacceptable level of $NO_2$ in the gas being directed to the recipient, or a combination thereof.

Embodiments of the present invention also relate to systems and methods of calibrating an integrated $NO_2$ sensor, and determining if an integrated $NO_2$ sensor is out of calibration, wherein an alarm may be generated and/or the reactor cartridge or delivery system may be placed into a non-functional state.

Embodiments of the present invention also relate to a reactor cartridge comprising an integrated pressure sensor for detecting the differential pressure of gases entering and exiting the $NO_2$-to-NO reactor cartridge, and a meter to measure the differential pressure across the cartridge.

Embodiments of the present invention also relate to a reactor cartridge comprising an integrated hygrometer ($H_2O$) sensor for detecting the moisture content of gases entering and/or exiting the $NO_2$-to-NO reactor cartridge, and a meter to measure the moisture level of the cartridge.

In addition, embodiments of the present invention relate to a reactor cartridge comprising an integrated accelerometer and/or orientation sensor for detecting the movement and/or angle of inclination of the cartridge, for example from a vertical position.

Principles and embodiments of the present invention relate generally to a system for safely delivering a supply of NO to a recipient, comprising a gas source that supplies a gas, wherein the gas comprises one or more of $NO_2$ or NO; a gas conduit connected to and in fluid communication with the gas source; a $NO_2$-to-NO reactor cartridge connected to and in fluid communication with the gas conduit, so as to allow gas to flow from the gas source to an inlet end of the reactor cartridge; a flow meter connected to and in fluid communication with the inlet end of the reactor cartridge and gas conduit to monitor the amount of gas delivered to the reactor cartridge; a delivery conduit connected to and in fluid communication with an outlet end of the conversion reactor that allows NO gas from the conversion reactor to flow to a recipient; a valve connected to and in fluid communication with the delivery conduit to close off the flow of gas to the recipient, and configured to receive an actuating signal from the computer; a computer in electronic communication with the flow meter over a communication path, and in electronic communication with the valve, wherein the computer is configured to receive electronic signals from the flow meter and calculate a usage value for comparison with a predetermined threshold value, and configured to generate an actuating signal when the usage value reaches the threshold value, and communicate the actuating signal to the valve to close and stop the flow of gas to the recipient.

In addition, embodiments of the present invention relate to a system which further comprises an outer housing encasing the gas source, wherein the outer housing is large enough to encapsulate the gas source and form an internal volume between the inside of the outer housing and the gas source.

In addition, embodiments of the present invention relate to a system which further comprises an absorbent material held within the internal volume which is sufficient to react with all of the material potentially released from the gas source.

In addition, embodiments of the present invention relate to a system which further comprises color agents intermixed with the absorbents, so that a color change of the color agent occurs when the absorbent interacts with the $NO_2$.

In addition, embodiments of the present invention relate to a system which further comprises an $NO_2$ sensor operationally associated with the delivery conduit to determine the presence of an unacceptable level of $NO_2$ in the gas being directed to the recipient.

In addition, embodiments of the present invention relate to a system which further comprises an impact sensor operationally associated with the reactor cartridge to determine the level of shocks sustained by the reactor cartridge.

In addition, embodiments of the present invention relate to a system which further comprises a memory chip operationally associated with the reactor cartridge to store reactor cartridge data on a non-transient computer readable medium, and wherein the memory chip is configured to be in electronic communication with the computer.

Embodiments of the present invention relate to a system, wherein the computer is configured to be in electronic communication with the memory chip over a communication path, and can read the reactor cartridge data stored on a non-transient computer readable medium; and wherein the computer is configured to communicate the actuating signal to the valve to close and stop the flow of gas to the recipient if the reactor cartridge data indicates the reactor cartridge is inoperable.

In addition, embodiments of the present invention relate to a system which further comprises a cartridge installation detector in electronic communication with the computer over a communication path that identifies when the reactor cartridge is properly coupled to the gas conduit and delivery conduit, and sends an actuating signal to the computer when the proper coupling of the reactor cartridge is detected; and wherein the computer prevents the gas delivery system from entering an operational state until an actuating signal is received from the cartridge installation detector.

Embodiments of the present invention relate to a system, wherein the computer is configured to receive electronic signals from the flow meter and calculate a usage value, and store the calculated usage value on the non-transient computer readable medium of the microchip for later reference, and wherein the computer prevents the gas delivery system from entering an operational state if the calculated usage data stored on the non-transient computer readable medium equals or exceeds the stored average expected lifetime of the reactor cartridge.

Principles and embodiments of the present invention relate generally to a reactor cartridge for converting $NO_2$ to NO, comprising an outer reactor shell; an inlet end wall that seals the inlet end of the reactor; an outlet end wall that seals the outlet end of the reactor to form an internal volume within the reactor cartridge; an inlet that facilitates connection of the reactor cartridge to a first gas conduit and allows passage of gas through the inlet end wall to the internal volume; an outlet that facilitates connection of the reactor cartridge to a second gas conduit and allows passage of gas through the outlet end wall to exit the reactor cartridge; a consumable conversion media retained within the internal volume of the reactor cartridge that facilitates conversion of an incoming $NO_2$ gas delivered to the inlet to an outgoing NO gas exiting at the outlet; a back end retainer positioned towards the outlet of the reactor cartridge to prevent consumable conversion media from exiting the internal volume of the reactor cartridge through the outlet; a front end retainer positioned towards the inlet of the reactor cartridge to prevent consumable conversion media from exiting the internal volume of the reactor cartridge through the inlet, wherein the consumable conversion media is retained between the front end retainer and the back end retainer; and a force-applying member positioned between the inlet end wall and the front end retainer to apply a pressure to the consumable conversion media.

In addition, embodiments of the present invention relate to a reactor cartridge which further comprises a memory chip affixed to the outer reactor shell, wherein the memory chip stores data relating to the conversion cartridge that the chip is affixed to on a non-transient computer readable medium.

Embodiments of the present invention relate to a reactor cartridge, wherein the stored data includes identification data, testing data, and/or cartridge life data.

In addition, embodiments of the present invention relate to a reactor cartridge which further comprises an impact sensor affixed to and/or operatively associated with the reactor cartridge, wherein the impact sensor is configured to determine the number of impacts and/or the severity of the impact(s) experienced by the reactor cartridge.

In addition, embodiments of the present invention relate to a reactor cartridge which further comprises an inlet with a keyed or polarized cartridge connector and/or an outlet with a keyed or polarized cartridge connector, wherein the keyed or polarized inlet and/or outlet connectors interact with a mechanical interlock to ensure the reactor cartridge is installed with the correct orientation in a gas delivery system.

Principles and embodiments of the present invention relate generally to a method of testing reactor cartridges to determine an expected lifetime, comprising assembling a number of reactor cartridges, comprising; providing a plurality of conversion cartridge shells; placing a first retainer on a support within the shell to partition off a section of the internal space; introducing a volume of a consumable conversion media into at least a portion of the internal volume of the conversion cartridge; placing a second retainer within the shell, that is held in position against the volume of consumable conversion media by a force-applying member; closing an inlet end of the conversion cartridge shell with an inlet end wall, wherein an end of the force-applying member is in contact with the inlet end wall and an opposite end of the force-applying member is in contact with the second retainer, so that a force is applied to the volume of a consumable conversion media; and closing an outlet end of the conversion cartridge shell with an outlet end wall; randomly selecting a number of reactor cartridges from the plurality of assembled reactor cartridges, where the number of cartridges selected for testing is less than the number of cartridges assembled; installing a randomly selected reactor cartridge into a NO gas delivery system; testing the installed reactor cartridge by a process comprising flowing a gas containing a predetermined concentration of NO2 through the installed reactor cartridge; measuring the amount of NO2-containing gas fed into the reactor cartridge with a flow meter; detecting the presence of NO2 at the outlet of the reactor cartridge; calculating the amount of NO2 converted to NO by the reactor cartridge up to the time NO2 was detected at the outlet of the of the reactor cartridge with a computer; and replacing the installed reactor cartridge with a subsequent randomly selected cartridge and repeating the testing process until all randomly selected reactor cartridges have been tested.

In addition, embodiments of the present invention relate to a method of testing reactor cartridges which further comprises calculating the amount of consumable conversion media used up to convert the amount of $NO_2$ converted to NO; averaging the calculated amount of consumable conversion media used up for each tested reactor cartridge; calculating the average amount of $NO_2$ that would be converted to NO for the untested plurality of assembled conversion cartridges.

In addition, embodiments of the present invention relate to a method of testing reactor cartridges which further comprises affixing a memory chip comprising a non-transient computer readable medium, and configured to communicate with a computer, to each of the conversion cartridge shells; and storing the average amount of NO2 that would be converted to NO on the non-transient computer readable medium.

In addition, embodiments of the present invention relate to a method of testing reactor cartridges which further comprises measuring the amount of $H_2O$ present in the consumable conversion media with a $H_2O$ sensor, and comparing the measured amount of $H_2O$ against a predetermined acceptable range for the reactor cartridge.

In addition, embodiments of the present invention relate to a method of testing reactor cartridges which further comprises measuring the differential gas pressure across the consumable conversion media to determine if there is a low pressure differential due to channeling or a crack in the conversion media.

Principles and embodiments of the present invention also relate to a method of monitoring the performance of an $NO_2$-to-NO reactor cartridge, comprising, providing an $NO_2$-to-NO reactor cartridge comprising a conversion media, incorporating one or more sensor probe(s) into the reactor cartridge and/or delivery system, wherein the one or more sensor probes are operatively associated with conversion media, providing a computer in electronic communication with the meter, providing at least one meter operatively associated with at least one sensor probe, and in electrical communication with the computer, detecting physical and/or chemical characteristics of the conversion media with the sensor probe(s), measuring the detected physical and/or chemical characteristics with the operatively associated meter, communicating the measured physical and/or chemical characteristics to the computer; monitoring the communicated characteristics with the computer; and displaying the measured characteristic(s) and/or activating and alarm.

BRIEF DESCRIPTION OF THE DRAWINGS

Further features of embodiment of the present invention, their nature and various advantages will become more apparent upon consideration of the following detailed description, taken in conjunction with the accompanying drawings, which are also illustrative of the best mode contemplated by the applicants, and in which like reference characters refer to like parts throughout, where.

DETAILED DESCRIPTION

Figure 1A:
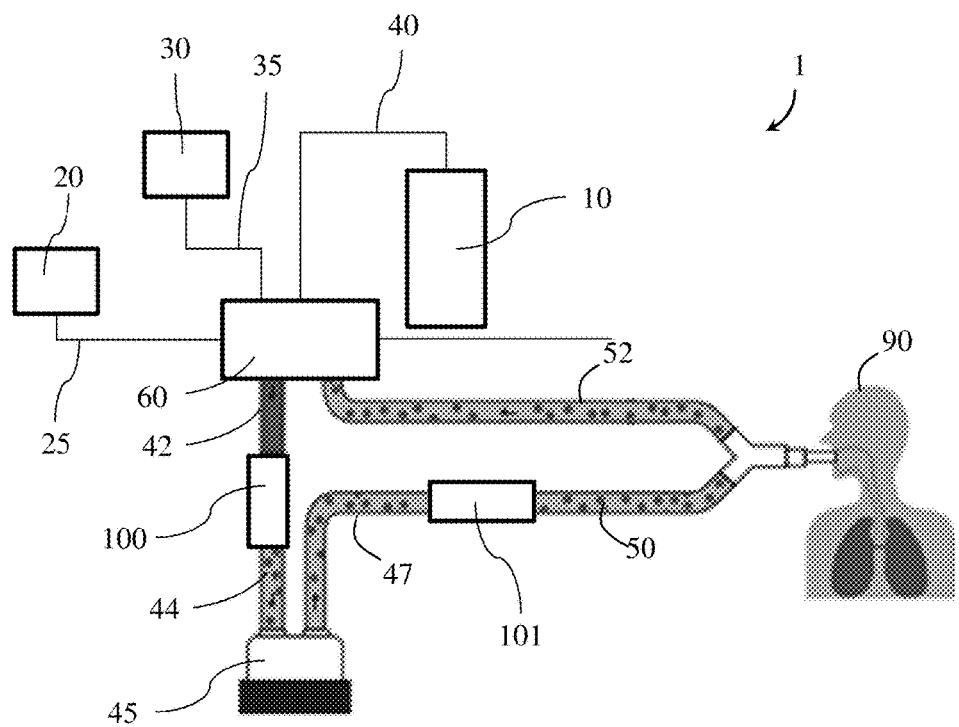
FIGS. 1A-1B illustrates exemplary inhalation therapy systems, in accordance with exemplary embodiments of the present invention.

The principles and embodiments of the present invention relate to methods and systems for safely providing NO to a recipient for inhalation therapy. As described above, there are many potential safety issues that may arise from using a reactor cartridge that converts $NO_2$ to NO, including errors and manufacturing deviations in the preparation of the cartridge reactor and of consumable reactants. Accordingly, various embodiments of the present invention provide systems and methods of manufacturing, storing, and installing a $NO_2$-to-NO reactor cartridge to alleviate the potential cartridge failure.

In embodiments of the present invention, the chemical and physical characteristics of the cartridge reactor and consumable reactants can be measured by suitable techniques including but not limited to volumetric and mass flow rates through the cartridge, spectroscopic analysis of consumable reactants, inert products, and/or gases, sampling and chromatography of gases, wet chemical analysis and/or quantitative detection of consumable reactants and/or gases, electrochemical analysis by voltammetry and/or amperometry, and/or quantitative or qualitative detection of consumable reactants by color change.

In embodiments, meters can detect and/or measure various characteristics of the conversion reactor and/or gas streams, including but not limited to the concentration of ascorbic acid, the concentration of dehydroascorbic acid, the concentration of water ($H_2O$), the concentration of $NO_2$, the concentration of NO, the concentration of $O_2$, the concentration of $HNO_3$, the pH of at least a portion of the conversion reactor or water vapor exiting the reactor, the redox potentials of chemical species in the conversion reactor, the mass flow rate of gases, the conductance at the surface of the silica gel, and the humidity of incoming and outgoing gases.

Various metering devices, apparatus, and methods have been further described in "SYSTEMS AND METHODS FOR INDICATING LIFETIME OF AN $NO_2$-to-NO REACTOR CARTRIDGE USED TO DELIVER NO FOR INHALATION THERAPY TO A PATIENT."

Various embodiments of the present invention can be used, modified, and/or be affiliated with various systems for delivering a pharmaceutical gas to a patient receiving inhalation therapy. These systems can include, but are not limited to, ventilators, CPAP/BiPAP and APAP systems, pulsed delivery systems, breathing circuits, nasal cannulas, breathing masks, and/or any other system for delivering a pharmaceutical gas to a patient receiving inhalation therapy.

Generally speaking, to provide NO inhalation therapy to patient in need thereof, these systems can include, but are not limited to, a source of gas that can provide NO as a final product, a source of air flow, a source of oxygen, a conduit that contains and/or communicates the gas and air flow to a $NO_2$-to-NO reactor cartridge, a delivery conduit that contains and communicates the NO gas and air mixture from the conversion reactor to a recipient interface.

Figure 1B:
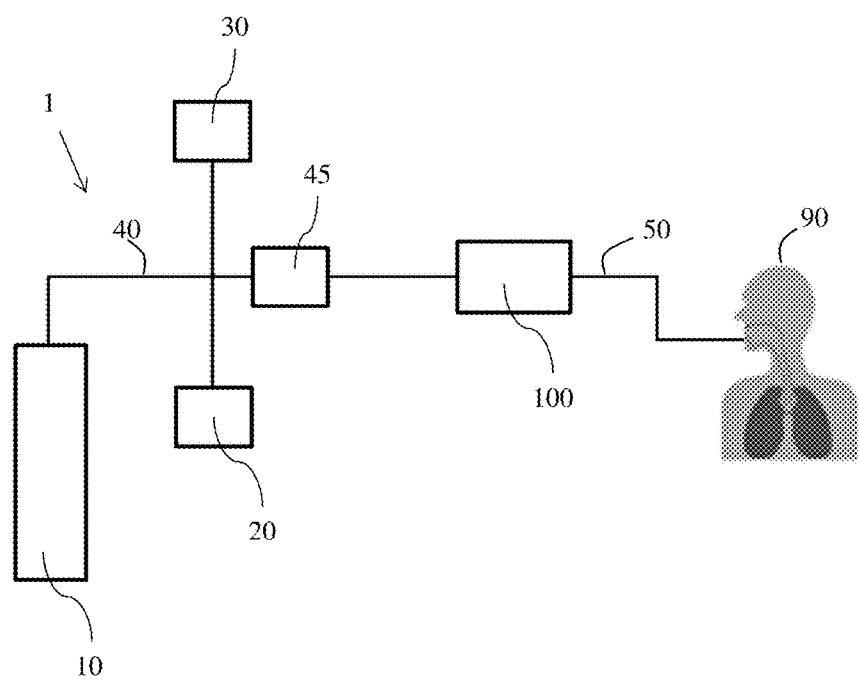

Referring to FIGS. 1A-1B, exemplary NO delivery systems are illustrated.

As shown in FIG. 1A, the embodiment of a NO gas delivery system 1 comprises a source of gas 10 connected to and in fluid communication with a ventilator 60 via a gas source conduit 40 that can contain and direct the gas from the gas source 10 to the ventilator 60. The ventilator 60 may provide a regulated flow of gas through the delivery system 1 to the recipient 90, which may have different specified flow patterns. An air supply 20, which may be an air pump, compressor, or centralized air supply, for example wall air in a hospital, also may be connected to and in fluid communication with the ventilator 60 via a gas conduit 25. An optional supply of oxygen 30 may also be connected to and in fluid communication with the ventilator via a gas conduit 35, where the oxygen supply may augment the concentration of oxygen delivered to a recipient 90. The air, $NO_2$, and/or $O_2$, may be mixed prior to entering the ventilator 60 or within the ventilator. The ventilator 60 may be connected to and in fluid communication with the gas source conduit 42, which can contain and direct the gas from the ventilator 60 to a first conversion reactor 100. The first conversion reactor 100 may be connected to and in fluid communication with the gas source conduit 42 at an inlet side, and connected to and in fluid communication with a gas source conduit 44 at an outlet side. A humidifier 45 may be connected to and in fluid communication with the gas source conduit 44 at an inlet side, and connected to and in fluid communication with the gas source conduit 47 at an outlet side. The gas source conduit 47 may contain and direct the gas from the humidifier 45 to a second conversion reactor 101, which may be the same as or different from conversion reactor 100. A gas delivery conduit 50 may be connected to and in fluid communication with the second conversion reactor 101 to contain and direct the gas from the outlet of the second conversion reactor 101 to the recipient 90. A ventilator conduit 52 may be connected to and in fluid communication with a ventilator 60, and interfaced with the gas delivery conduit 50, and/or recipient 90, for example with a Y-tube.

In embodiments, the humidifier helps maintain an acceptable level of moisture in the air/NO gas supply entering the second conversion reactor 101 to ensure a sufficient amount of $H_2O$ for the reactor to function properly.

In embodiments, the second conversion reactor 101 converts any $NO_2$ that failed to be converted by conversion reactor 100 and/or that has formed in the conduits and humidifier through reaction of NO with $O_2$ or $H_2O$ back into NO before $NO_2$ in the gas stream reaches a recipient 90.

In embodiments, a computer system may be connected to and in electrical communication with a ventilator 60, as well as automatic valves and regulators (e.g., pressurized air, solenoid, and solenoid pneumatic valves), and various meters and detectors (e.g., flow meters, $NO_2$ detector, $H_2O$ detector, etc.).

As shown in FIG. 1B, another non-limiting embodiment of a NO gas delivery system 1 comprises a source of gas 10, which may be a $NO_2$ gas source, which can be connected to and in fluid communication with gas source conduit 40 that can contain and direct the gas from the gas source 10 to a conversion reactor 100. A humidifier 45 may be connected to and in fluid communication with the gas source conduit 40, and inserted between the gas source 10 and conversion cartridge 100 to add moisture (i.e., $H_2O$) to the gas entering the conversion cartridge 100. An air supply 20, which may be an air pump, compressor, or wall air, may be connected to and in fluid communication with the gas source conduit 40 to provide a flow of ambient air with the $NO_2$ source gas. An optional supply of oxygen 30 may also be connected to and in fluid communication with the source conduit 40, for example, to supplement the amount of oxygen being fed through the conduit(s). The source conduit 40 can be connected to and in fluid communication with the conversion reactor 100, which in turn can be connected to and in fluid communication with a gas delivery conduit 50 that contains and directs the gas from the conversion reactor to a patient 90. In embodiments, an NO gas source (not shown) may be connected to and in fluid communication with the source conduit 40, alone or in combination with the $NO_2$ gas source, as a backup.

Principles and embodiments of the present invention also relate to providing protective elements operatively associated with a source of $NO_2$, and/or a reactor cartridge, which may comprise components to absorb any $NO_2$ that may leak out of the $NO_2$ source and/or reactor cartridge, and color agents that indicate the presence of $NO_2$.

Figure 2:
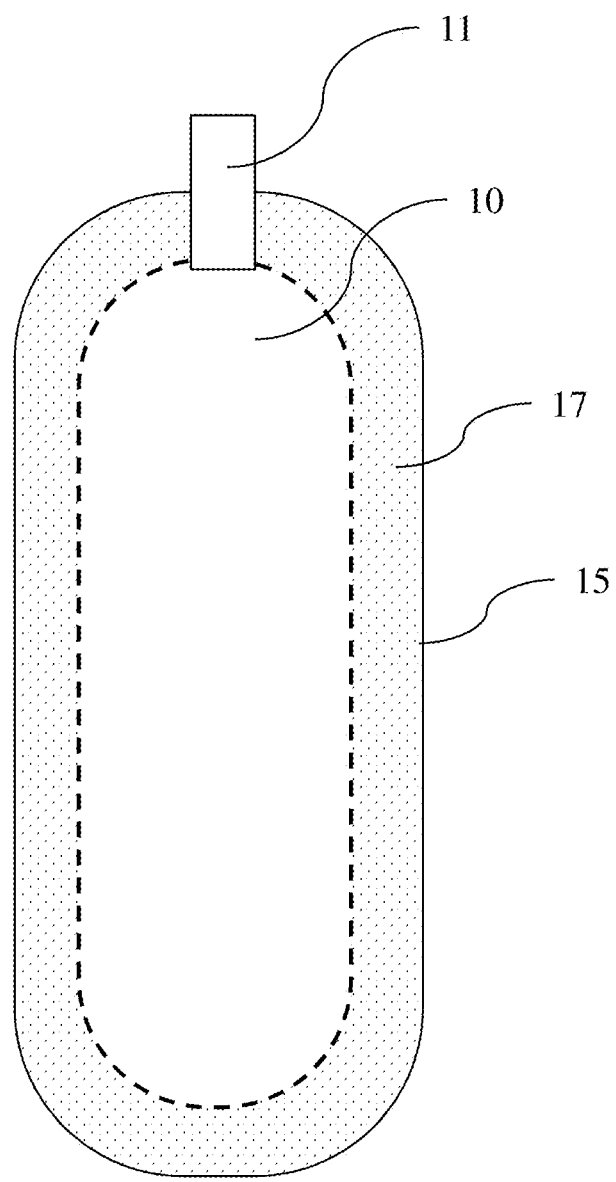
FIG. 2 illustrates an exemplary housing around a source of $NO_2$, in accordance with exemplary embodiments of the present invention.

In various embodiments, as shown in FIG. 2, a source of $NO_2$ gas 10 may be encased within an outer housing 15 that surrounds the container holding the $NO_2$ source material (e.g., $NO_2$ gas, $N_2O_4$ liquid, and gas, liquid, or solid, which may react to produce $NO_2$, etc.). The $NO_2$ gas container 10 and/or outer housing 15 may be glass, quartz, silica, steel, stainless steel, anodized aluminum, chemically resistant alloys (Waspaloya, fluoro-polymers (e.g., Teflon®), and combinations thereof (e.g., glass or fluoro-polymer lined stainless steel or aluminum). In embodiments of the present invention, the outer housing 15 can be large enough to encapsulate the $NO_2$ source container 10 or a reactor cartridge to reduce or prevent any $NO_2$ gas from reaching the atmosphere, and form an internal volume between the inside of the outer housing and the $NO_2$ source container sufficiently large to hold enough absorbent 17 to react with all of the gas or liquid possibly released from the $NO_2$ source container 10. The size of the housing and amount of absorbent would be related to the size of the $NO_2$ source container and amount of $NO_2$ potentially generated. Reaction between the $NO_2$ source gas or liquid and the absorbent should be complete, such that none of the $NO_2$ remains after interacting with the absorbent. A surplus of absorbent may be included to provide a safety factor to ensure all of the $NO_2$ is absorbed and/or reacted. A valve and feed line 11 may be connected to and in fluid communication with the $NO_2$ gas container 10, and pass through the outer housing 15 in a manner that forms a gas-tight seal (e.g., welding, brazing, gaskets, epoxies, etc.).

In embodiments of the present invention, the $NO_2$ may be absorbed by absorbents, including silica gel, alumina, soda lime, activated carbon/charcoal, and magnesium sulfate.

In embodiments of the present invention, the absorbents may be treated and/or intermixed with the color agents, so that a color change of the color agent occurs when the absorbent interacts with the $NO_2$ or when at least a portion of the absorbent is used up. In embodiments of the invention, the presence of $NO_2$ may be indicated by a color agent, which may be for example sulfanilic acid (diazotizing agent) in combination with N(1-naphthyl)ethylene diamine dihydrochloride, metalloporphyrins, for example (5,10,15,20-tetrraphenylporphyrin)-zinc, ethyl violet, and malachite green. In a non-limiting example, in the absence of $NO_2$ sulfanilic acid (diazotizing agent) in combination with N(1-naphthyl)ethylene diamine dihydrochloride has white color but yields light purple color at about 3.7 ppm and medium purple at about 10 ppm of $NO_2$. In a non-limiting example, metalloporphyrins may change from purple to yellow. In embodiments, the color agent may also indicate changes in pH that occurs upon exposure to $NO_2$.

In embodiments, the outer housing may be transparent (e.g., glass, quartz, fused quartz, polycarbonate) or have an opening in the non-transparent material body (e.g., steel) with a transparent window (e.g., glass, quartz, fused quartz, polycarbonate), so that a user may observe any color change by the color change agent.

In embodiments of the present invention, the $NO_2$-to-NO reactor cartridge, also referred to as a conversion reactor or conversion cartridge, can include an outer reactor shell or body, an inlet, an outlet, and a consumable conversion media including solid packing material coated with consumable reactant, for example an antioxidant and water, where the solid packing material can be retained within the internal volume of the reactor shell, and where the coated packing material provides a consumable reactant surface. The solid packing material and consumable reactant coating form a consumable conversion media. In one or more embodiments, the antioxidant is ascorbic acid, which can be applied to the packing material in an aqueous solution, and the packing material may be silica gel. Other antioxidants include suitable reducing agents for the conversion of $NO_2$ to NO, such as alpha tocopherol and gamma tocopherol. Other packing material may include calcium sulfate dehydrate, calcium fluorophosphate dihydrate, zirconium (IV) oxide, zircon, titanium dioxide, and aluminum silicate, or any suitable material that can be coated with consumable reactant and/or that can be hydrated.

In embodiments of the present invention, the agents for the conversion of $NO_2$ to NO also may be toluidine, benzidine, and benzidine derivatives, as presented in U.S. Pat. No. 3,106,458 issued on Oct. 8, 1963, to Grosskopf et al., and incorporated herein by reference in its entirety. The benzidine may be for example N,N,N,N'-tetraphenylbenzidine, N,N'-dimethyl-N,N' diphenylbenzidine, or N,N' diphenylbenzidine, which may be combined with a strong acid on a carrier, such as silica gel, as a reagent for $NO_2$. The toluidine, benzidine, and benzidine derivatives may be deposited onto the carrier and exposed to $NO_2$, and the toluidine, benzidine, and benzidine derivatives undergo a color change upon such exposure. In embodiments the reaction between $NO_2$ and the aromatic amines produces NO and a reactant product. For example, the N,N' diphenylbenzidine can react with $NO_2$ to produce NO, $H_2O$, and NN-diphenyl-1,4-phenylenediamine.

Figure 3A:
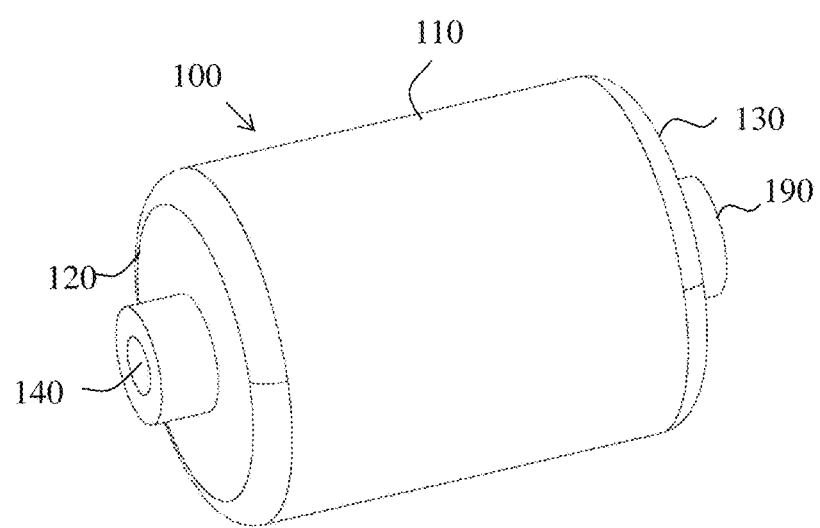
FIGS. 3A-3C illustrate an exemplary $NO_2$-NO conversion reactor, in accordance with exemplary embodiments of the present invention.
Figure 3B:
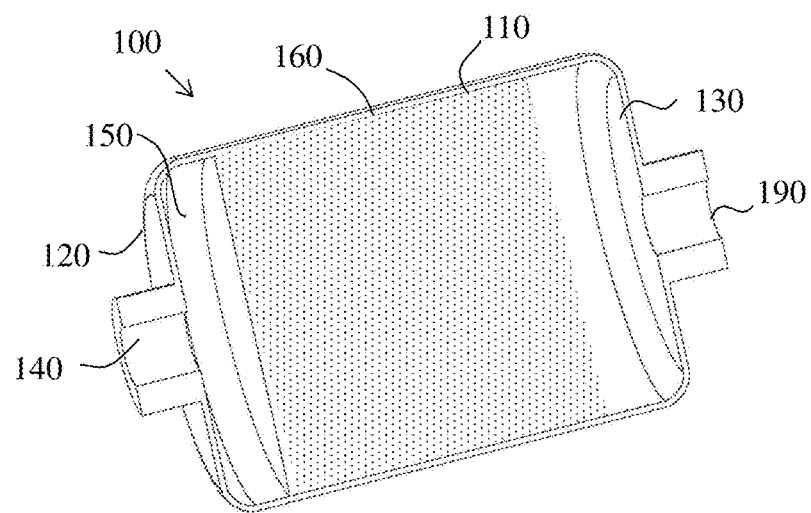
Figure 3C:
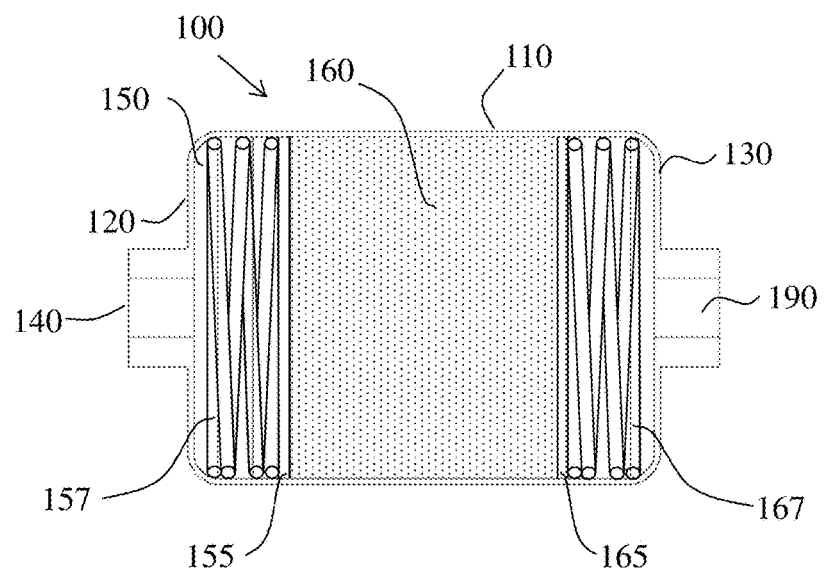

Referring to FIGS. 3A-3C, a general example of a packed-type $NO_2$-to-NO reactor cartridge 100 is illustrated. The conversion reactor, as shown in FIG. 3A has a body with an outer annular wall 110, an inlet end wall 120 that seals the inlet end of the reactor, an outlet end wall 130 that seals the outlet end of the reactor to form an internal volume 150 within the reactor 100. The reactor also has an inlet 140 that facilitates connection of the reactor 100 to a gas conduit (not shown) and allows passage of gas through the inlet end wall 120 to the internal volume 150. An outlet 190 facilitates connection of the reactor 100 to another gas conduit (not shown) and allows passage of gas through the outlet end wall 130 to be delivered to a recipient. At least a portion of the internal volume 150 of the reactor 100 may contain a consumable conversion media 160 that facilitates conversion of an incoming $NO_2$ gas delivered to the inlet 140 to an outgoing NO gas exiting at the outlet 190.

In embodiments, the inlet and/or outlet may comprise a connector that is keyed or polarized, so that the cartridge can only be installed with the correct orientation and gas flow direction. The conduits 40,42,47,50 may also comprise a mating connector that is keyed or polarized to match the particular connector on the cartridge. In embodiments, cartridges 100,101 may comprise connectors with different keying/polarization features, so that reactor cartridge 100 may not be interchanged or substituted with a reactor cartridge 101, and vise versa.

As shown in FIG. 3B, the embodiment of a $NO_2$-to-NO reactor cartridge 100 comprises a consumable conversion media 160 comprising a flowable, granular or pelletized solid material that fills at least a portion of the internal volume formed by the annular wall 110 of the reactor cartridge 100. In embodiments, the consumable conversion media 160 may not fill the entire volume of the reactor cartridge, so empty spaces may be left towards the inlet side and/or outlet side of the cartridge.

As shown in FIG. 3C, the embodiment of a $NO_2$-to-NO reactor cartridge 100 may comprise a front end retainer 155 positioned nearer the inlet 140 and a back end retainer 165 opposite the front end retainer 155 and positioned nearer to the outlet 190 of the reactor. In embodiments, a front end compression spring 157 may be positioned between the front end wall 120 and the front end retainer 155 to apply a pressure against the otherwise flowable packing material to compact it. In embodiments, a back end compression spring 167 may be positioned between the back end wall 130 and the back end retainer 165 to apply a pressure against the otherwise flowable packing material to compact it. The retainers 155,165 and optionally one or more compression springs 157,167 hold the consumable conversion media in place against shocks, vibration and handling, so it does not shift and/or form channels. The retainers should be sufficiently porous to permit gas to flow through without significant pressure drop relative to the pressure drop caused by the consumable conversion media and/or the gas pressure provided by various embodiments of the system 1.

Although reference for the embodiment has been made to compression springs, this is for convenience, and other mechanisms may be employed to apply a pressure to the retainer(s), including but not limited to wave washers, compression washers, an elastomeric sleeve, foam, or one or more of O-rings, which would take up a similar limited space and also be compatible with the operating environment, which may be referred to as force-applying member(s) and are considered within the scope of the present invention.

Although reference has been made to an annular or cylindrical wall, other shapes including but not limited to oval, elliptical, quadrilateral, and polygonal, are also contemplated and intended to fall within the scope of the invention. The general shape of the reactor cartridge, internal volume, and monolithic conversion media may be altered without deviating from the scope of the present invention.

Figure 4A:
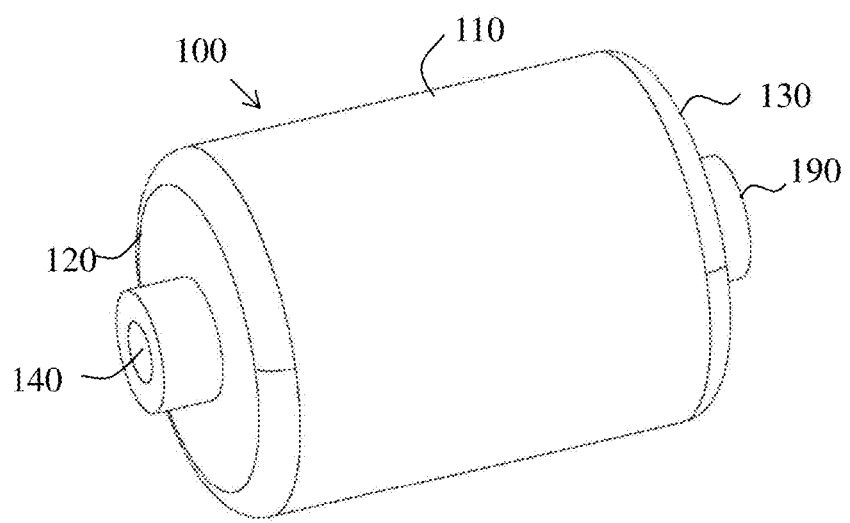
FIGS. 4A-4C illustrate another exemplary $NO_2$-NO conversion reactor, in accordance with exemplary embodiments of the present invention.
Figure 4B:
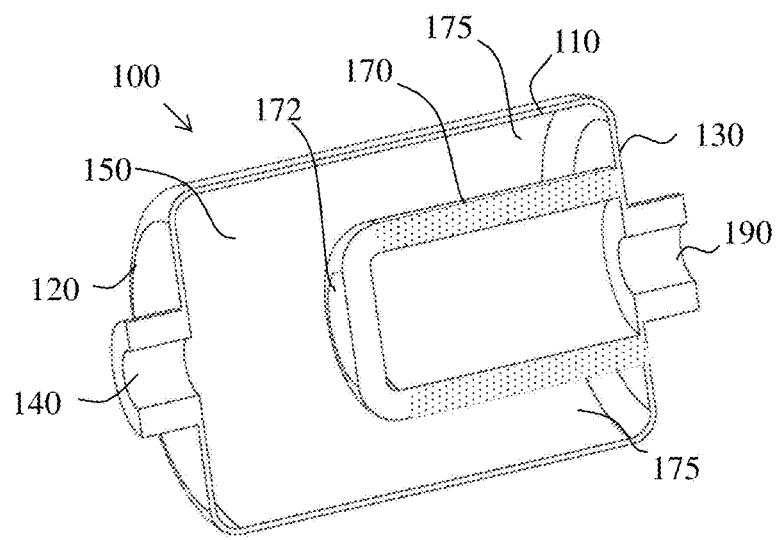
Figure 4C:
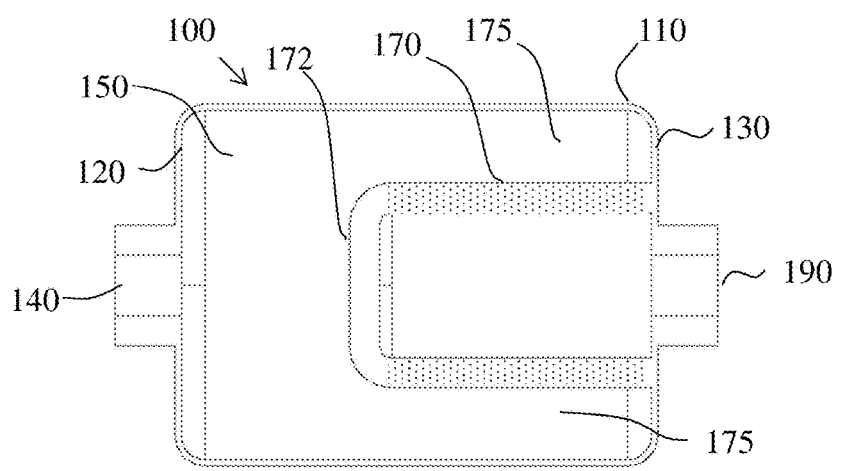

Referring to FIGS. 4A-4C, a general example of porous solid-type $NO_2$-to-NO reactor cartridge 100 is illustrated. The conversion reactor 100, as shown in FIG. 4A, may also comprise an outer annular wall 110, inlet end wall 120, outlet end wall 130, inlet 140 and outlet 190, and may have a similar configuration and dimensions as a cartridge with a packed solid conversion media 160. However, differing from the above described packed-type $NO_2$-to-NO reactor cartridge, the consumable conversion media for the porous solid-type $NO_2$-to-NO reactor cartridge 100 can be a coated porous, bonded or sintered structure, for example a glass frit or sintered silica gel, in the form of a porous, cylindrical wall 170 to provide a surface area for coating with the consumable reactant, for example ascorbic acid and water. An example of a sintered silica gel is described in U.S. Pat. No. 3,397,153 A issued Aug. 13, 1968, to Sippel et al., and incorporated herein by reference in its entirety.

Referring to FIGS. 4B-4C, a first end of the cylindrical wall 170 may be capped with an end wall 172 of similar porous material or closed off with a non-porous disk. The second end of the cylindrical wall opposite the first end may be affixed to the outlet end wall 130, such that the cylindrical wall 170 surrounds the outlet 190. Gas entering the conversion reactor 100 through the inlet 140 enters the internal volume 150 of the reactor body including the gap 175 between the outer annular wall 110 and the porous cylindrical wall 170, and is forced through the porous cylindrical wall 170 under pressure, as may be produced by a system 1. The porous cylinder wall 170 is affixed to the outlet end wall 130 in a manner that prevents gas from penetrating between the cylindrical wall and end wall, as would be known in the art of bonding technology, so all of the gas exiting the cylinder should pass through the porous cylindrical wall 170. A porous cylindrical wall coated with consumable reactants forms a monolithic consumable conversion media in contrast to a packed consumable conversion media, wherein monolithic refers to a structure having a defined shape and determinable dimensions in contrast to a packed material formed by a large number of separate particles that flow if not retained within a volume.

In various embodiments, the consumable conversion media, therefore, can be a cylindrical wall or a packed bed coated with the consumable reactants. The reactant gas (e.g., $NO_2$), may become absorbed onto the coated surface (e.g., silica gel) and interact with the consumable reactants (e.g., ascorbic acid and water) to produce a product gas (e.g., NO), which desorbs from the surface of the consumable conversion media and is transported out of the conversion reactor by a carrier gas, which may be non-reactive (e.g., $N_2$), reactive (e.g., $O_2$, $H_2O$), or a combination thereof (e.g., air).

In various embodiments, the porous cylindrical wall 170 may comprise one or more binders and/or reinforcements to increase the structural strength and integrity of the porous cylindrical wall 170 to stresses, strains, and impacts above the value the wall would have without such additional features. In various embodiments, the reinforcements may be carbon fibers, glass fibers, aramid fibers, mica, and high strength ceramics (e.g., silicon nitride, silicon-aluminum oxy nitride (sialon), silicon carbide, boron carbide, etc.), or a combination thereof, and the binders, also referred to as a matrix, may be polyesters, epoxies, polyethylene, polypropylene, nylon, and vinyl esters, or a combination thereof.

In various embodiments, the reinforcement and/or binder(s) may be incorporated into the silica to increase the composite's strength and resistance to impacts. In embodiments, the reinforcement and/or binder(s) may be incorporated into the silica in an amount in the range of about 2 wt % to about 30 wt %, or alternatively in the range of 5 wt % to 20 wt %, or about 10 wt % to 15 wt %. In embodiments, the size of the cylindrical wall 170 may be increased to compensate for surface area lost to the reinforcements and binders.

It will be understood that the cross-sectional shape of $NO_2$-to-NO reactor cartridges, and elements thereof, can be any reasonable cross-sectional shape such as, but not limited to, round, ovoid, quadrilateral, and polygonal, to name a few. For ease, the cross-sectional shape of $NO_2$-to-NO reactor cartridges, and elements thereof, is described as being round, or variations thereof. This is merely for ease and is in no way meant to be a limitation.

Figure 5A:
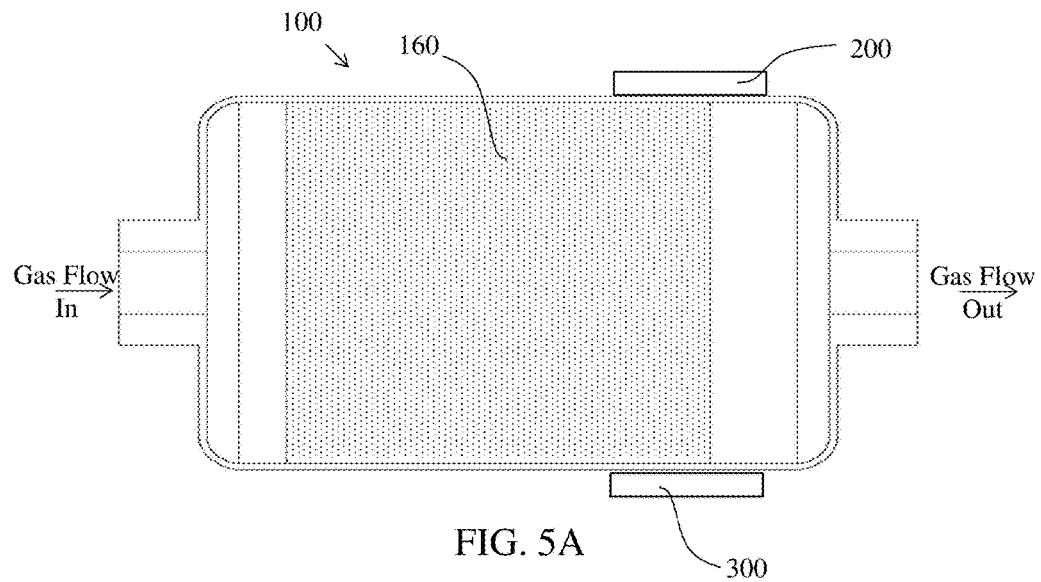
FIGS. 5A-5B illustrate exemplary $NO_2$-NO reactor cartridge, in accordance with exemplary embodiments of the present invention.
Figure 5B:
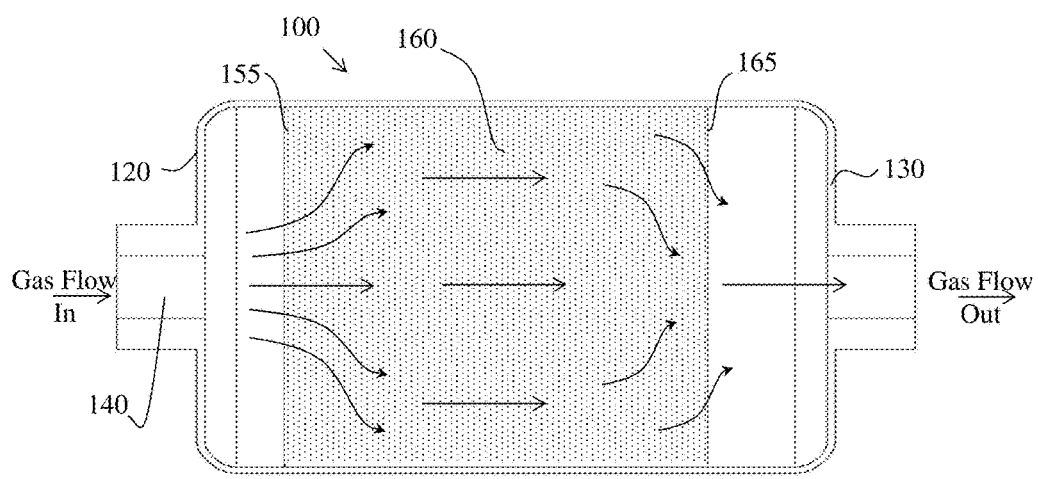

FIGS. 5A-5B illustrate a cut-away view of a conversion reactor 100 indicating the intended direction of gas flow through the internal volume 150 and packed consumable conversion media 160.

FIG. 5A illustrates a conversion reactor with an impact sensor 200 and a memory chip 300 affixed to and operatively associated with the reactor cartridge, wherein the impact sensor and/or memory chip may be configured to be in electronic communication with a computer.

In the embodiment illustrated in FIG. 5B, the packing material may be held within a portion of the internal volume by a front end retainer 155 positioned nearer the inlet 140 and a back end retainer 165 opposite the front end retainer 155 and positioned nearer to the outlet 190 of the reactor. There may be a gap between the inlet end wall 120 and the front end retainer 155 that does not contain any packing material and forms an open internal volume at the inlet 140. There may also be a gap between the outlet end wall 130 and back end retainer 165 that does not contain any packing material and forms an open internal volume at the outlet 190. A general direction of gas flow through the cartridge is indicated by arrows.

Figure 6:
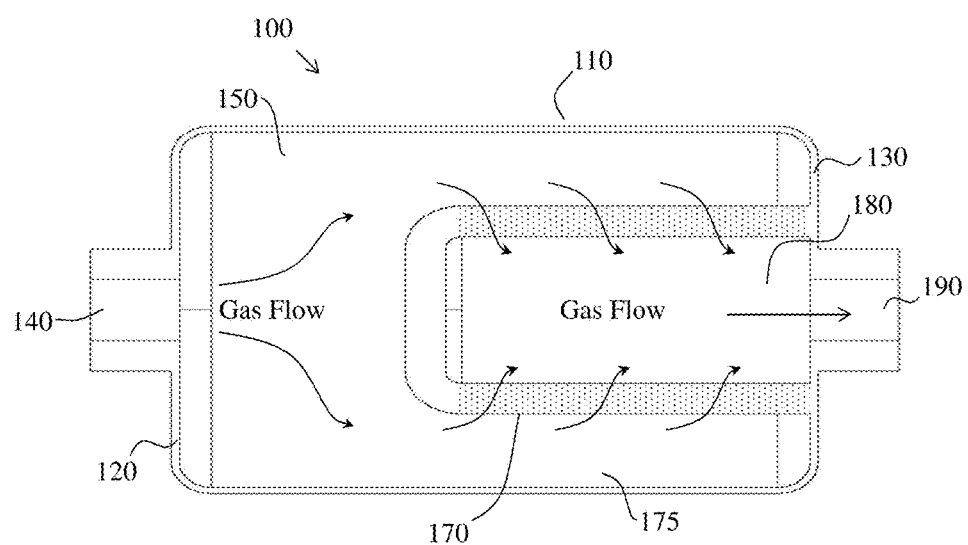
FIG. 6 illustrates an exemplary $NO_2$-NO reactor cartridge with a monolithic consumable conversion media showing gas flow, in accordance with exemplary embodiments of the present invention.

FIG. 6 illustrates a cut-away view of a conversion reactor 100 indicating the intended direction of gas flow through the internal volume 150 and cylindrical wall 170 of the monolithic consumable conversion media. The gas enters through the inlet 140 and passes through the internal volume 150 and gap 175 to the monolithic consumable conversion media, which can be semi-permeable. The gas passes through the porous cylindrical wall 170 of the semi-permeable, monolithic, conversion media into the hollow space 180 and out through the outlet 190. $NO_2$ gas passing through a consumable reactant coated cylindrical wall 170 can be converted into NO through interaction with consumable reactants (e.g., ascorbic acid and $H_2O$) on the surfaces. In exemplary embodiments, the thickness of the cylindrical wall should be greater than the mean free path of the gas through the porous wall material to ensure all of the $NO_2$ interacts with a consumable reactant coated surface before reaching the hollow space 180.

While the direction of gas flow has been illustrated as from the exterior of the semi-permeable wall 170 into the interior hollow space 180, in embodiments the direction may be reversed or in other directions without departing from the spirit and scope of the invention.

Principles and embodiments of the present invention relate to systems and methods of manufacturing a conversion cartridge comprising a consumable conversion media, an external shell of the conversion cartridge may be provided, where the external shell comprises a wall having a shape and an open internal space that can accommodate a predetermined weight or volume of conversion media. In embodiments a first retainer may be placed within the shell to partition off a section of the internal space to hold a packed material.

In various embodiments, a first retainer comprising a gas-permeable disk may be placed within the conversion cartridge shell, and may be held in position by a support, for example a shoulder, a plurality of protrusions, or a standoff. The retainer may have a shape that conforms to the internal shape of the shell. In embodiments, the retainer may be configured and dimensioned to fit snugly within the shell so that a gap between the retainer edge and cartridge wall is less than the dimensions of the packed material forming the conversion media. For example, if the conversion media is comprised of silica gel having a particle diameter of 100 microns, the clearance space between the retainer edge and the inside of the cartridge wall should be less than 100 microns to prevent the silica particles from circumventing the retainer. In embodiments, a flexible washer, gasket, or O-ring may be operatively associated with the retainer to fill or block the clearance space between the retainer edge and the inside of the cartridge wall.

In various embodiments, a force-applying member (e.g., compression spring) may be placed between a shoulder, protrusions, or a standoff, and the retained to apply a pressure to the retainer and compensate for decreases in volume of the packed conversion media.

In various embodiments, the consumable conversion media comprises a solid packing material, for example silica gel having a particle size of about 30 to about 1000 microns, or about 60 to 500 microns. The packing material may be in the form of a granular or pelletized flowable solid.

In embodiments, the solid packing material may be coated with consumable reactant, for example an antioxidant and water, where the packing material provides a surface for the consumable reactants.

Ascorbic acid has a solubility in water of 330 g/l. In embodiments utilizing ascorbic acid, up to 330 g/l may be dissolved in water to produce a solution for coating the solid packing material. In some embodiments, a saturated solution of ascorbic acid in water is used to prepare the consumable conversion media with the antioxidant and water.

Alpha—tocopherols are essentially insoluble in water, so would be applied neat or using a suitable organic solvent, for example acetone, to coat the solid packing material.

In various embodiments, a predetermined weight of antioxidant may be dissolved in a suitable carrier may be brought into contact with a predetermined weight or volume of solid packing material, and the solvent allowed to evaporate, so the predetermined weight of antioxidant is deposited onto the surface of the packing material.

In various embodiments, a predetermined weight of antioxidant may be dissolved in a predetermined amount of solvent to provide a solution of predetermined concentration. An amount of the solution may be passed through a predetermined weight or volume of solid packing material, and excess solution drained from the packing material, which may then be dried, so a predetermined weight of antioxidant is deposited onto the surface of the packing material.

In embodiments, the coated packing material provides a flowable form of consumable conversion media, which may be introduced into at least a portion of the internal volume of the conversion cartridge. A specific weight or volume of consumable conversion media may be poured into a conversion cartridge, which already has a first retainer suitably positioned in the cartridge to prevent passage of the conversion media out of the internal volume or even the cartridge outlet.

In various embodiments, a second retainer comprising a gas-permeable disk may be placed within the conversion cartridge shell, and may be held in position against a volume of consumable conversion media by a force-applying member (e.g., compression spring), which places a force on the second retainer to assist in compacting and maintaining the consumable conversion media within the predetermined internal volume. The retainer may have a shape that conforms to the internal shape of the shell. In embodiments, the retainer may be configured and dimensioned to fit snugly within the shell so that a gap between the retainer edge and cartridge wall is less than the dimensions of the packed material forming the conversion media.

In various embodiments, the shell of the conversion cartridge may be closed at each end with an end wall, such that the intended outlet side of the cartridge is sealed by an outlet end wall and the opposite or inlet side of the cartridge is sealed by an inlet end wall. The inlet and wall and outlet end wall may have inlet and outlet openings to allow gas(es) to enter and exit the reactor cartridge.

In various embodiments, the one or more force-applying member(s) may be held in position and be compressed against the respective end wall to provide suitable pressure against the particles of the consumable conversion media, so the media is held in place over an extended period of time.

In various embodiments relating to a method of manufacturing a semi-permeable, monolithic, consumable conversion media and conversion cartridge, a predetermined weight of antioxidant may be dissolved in a suitable carrier and coated onto a porous cylindrical wall of sintered or bonded packing material to form a monolith conversion media. The monolith conversion media may be bonded to the outlet end wall 130 to form a gas-tight seal, and the outlet end wall sealed to the annular cartridge wall 110 to form a gas-tight seal. An inlet end wall may be sealed to the annular cartridge wall 110 to form a gas-tight seal.

It will be understood that principles and embodiments described with reference to porous solid-type $NO_2$-to-NO reactor cartridges, and elements thereof, and principles and embodiments described with reference to packed-type $NO_2$-to-NO reactor cartridge, and elements thereof, can, when applicable, be implemented in either configuration. This is merely for ease and is in no way meant to be a limitation. Accordingly, reference made to one type of reactor cartridge or another, at times, is made for ease and is not meant to be limited to that type of reactor cartridge.

When the reactor is configured as a packed column, incoming $NO_2$ interacts with the consumable reactant's active consumable conversion media closest to the reactor inlet first. As the conversion material is used up by exposure to the $NO_2$, additional incoming $NO_2$ passes further into the packed column before reaching an active surface of the consumable reactant. This process proceeds through the packed material until $NO_2$ can pass all the way through the reactor without interacting with a consumable reactant surface. At this point $NO_2$ breakthrough occurs, and the reactor is effectively depleted.

Breakthrough may be when $NO_2$ is at a concentration of about 0.1 ppm. 0.2 ppm, 0.3 ppm, 0.4 ppm, 0.5 ppm, 0.6 ppm, 0.7 ppm, 0.8 ppm, 0.9 ppm, 1 ppm, 1.5 ppm, 2 ppm, 2.5 ppm, 3 ppm, 3.5 ppm, 4 ppm, 4.5 ppm, 5 ppm, 6 ppm, 7 ppm, 8 ppm, 9 ppm or 10 ppm in the gas stream exiting the $NO_2$-to-NO reactor cartridge.

Principles and embodiments of the present invention also relate to a safety interlock system that may automatically identify a specific conversion cartridge when it is installed in a NO gas delivery system.

In embodiments, a memory chip may be affixed to a conversion cartridge, where the memory chip stores data relating to the specific conversion cartridge. In various embodiments, the stored data may include identification data, testing data, and/or cartridge life data.

In various embodiments, identification data may include for example a cartridge serial number, a lot and/or batch number, a production date, an expiration date, or a combination of such identification data. This identification data may be used to ensure usage of desired cartridges. For example, using this data, if cartridges (e.g., cartridge 100, cartridge 101) are from the same lot, batch, production date, expiration date, manufacturing facility, etc. are used an alarm may go off indicating to the user that they cannot use the cartridge and/or use of the cartridges may not be allowed.

In various embodiments, testing data may include for example a weight of consumable conversion media within the conversion cartridge, values of test results showing conversion efficiency of $NO_2$ to NO, pressure drop across the consumable conversion media, humidity level of the consumable conversion media, a pass or no-pass test rating for the cartridge, or a combination of such test data.

In various embodiments, cartridge life data may include for example average expected cartridge life calculated from test data, total expected $NO_2$ conversion by weight, concentration, and/or volume, expected duration of usage at an average gas flow rate, or a combination of such cartridge life data.

In various embodiments, the memory chip may comprise a non-transient computer-readable media, and a connector operatively associated with the non-transient computer-readable media over one or more electrical lines, where a computer controlling the NO gas delivery system is configured and adapted to connect to and electrically interact with the non-transient computer-readable media to read the stored data.

In various embodiments, the NO gas delivery system will not enter an operational state unless the computer controlling the NO gas delivery system can identify the installed conversion cartridge from the identification data stored in the non-transient computer-readable medium of the memory chip, and receives confirmation that the specific conversion cartridge has acceptable test values and/or a pass rating. In embodiments, the communication of data from the memory chip to the computer controller acts as at least a portion of a NO gas delivery system interlock. A conversion cartridge with an associated memory chip storing data that indicates for example that the cartridge has passed an expiration date, has marginal test results, or indicates that the consumable conversion media has previously been used up, may register as the reactor cartridge being inoperable.

In various embodiments, a cartridge installation detector may determine whether the conversion cartridge is properly coupled to the gas source conduit and the conversion cartridge is properly coupled to the delivery conduit. In embodiments, the cartridge installation detector may be a proximity switch, a leaf switch, or a closed-circuit detector that identifies a closed circuit when the cartridge is coupled to the conduit(s). In embodiments, the detection of the proper mechanical installation of the conversion cartridge acts as at least a portion of a NO gas delivery system interlock.

Without such an interlock, an $NO_2$ source may be activated with an open ended conduit and no reactor cartridge to convert the toxic $NO_2$ gas into NO before it is released.

In various embodiments, the keyed or polarized cartridge connectors interact with the mechanical interlock to ensure the cartridge is installed with the correct orientation in the gas delivery system.

In various embodiments, this interlock system effectively shuts down the NO gas delivery system until an identifiable and viable conversion cartridge is properly installed both mechanically and electronically in the gas delivery system.

In various embodiments, the NO gas delivery system may transmit usage data from the computer controller to the memory chip for storage in the non-transient computer readable medium. The usage data may include for example the weight, volume, and/or concentration of $NO_2$ that has been fed into the conversion cartridge while it was installed in the NO gas delivery system. The stored usage data may be read by a delivery system computer controller to determine the anticipated remaining life of the specific installed conversion cartridge based on the previous weight, concentration, and/or volume flow of $NO_2$ through the cartridge.

In various embodiments, the NO gas delivery system may not enter an operational state unless the computer controlling the NO gas delivery system can determine that the installed cartridge has a suitable remaining life time for the expected dosage and/or treatment time.

In various embodiments, the identification data, testing data, and/or cartridge life data may be printed as a 1-D or 2-D bar code label that may be physically affixed to a conversion cartridge, for example with an adhesive, and the NO gas delivery system will not enter an operational state unless the computer controlling the NO gas delivery system can read and identify the encoded cartridge from the affixed bar code, for example by scanning the bar code with a bar code reader in communication with the computer.

In various embodiments, a communication path may be a physical line (e.g., cooper wire, fiber optics) connected to two or more electronic devices that can carry an electronic signal, or a wireless communication path, for example radio communication, infrared communication, or microwave communication, that can convey an electronic signal between two or more electronic devices without a physical line connection.

Once a conversion cartridge has been manufactured, it may be tested to determine that it is operating properly. For example, it may be checked for the correct moisture content, the proper pressure drop between the inlet and outlet end, and $NO_2$ may be introduce to determine that the consumable media is suitably active, so that no $NO_2$ exits the cartridge.

In various embodiments, the moisture content of the conversion media in a sealed conversion cartridge may be tested with a moisture sensor within the cartridge and external leads or connectors that can be placed in communication with an appropriate meter was would be known in the art.

In various embodiments, a moisture sensor may be placed within a conduit connected to and in fluid communication with the outlet of a sealed conversion cartridge to determine the moisture content of the gas exiting the cartridge, and correlating the amount of evaporated moisture exiting the cartridge with the amount of moisture present in the consumable conversion media. The relationship between gas moisture and media moisture may have been previously determined through testing and statistical calculations.

With an understanding of the delivery systems and $NO_2$-to-NO reactor cartridges, principles and embodiments of the present invention relating to systems and methods of determining the remaining useful life of a $NO_2$-to-NO reactor cartridge and/or a breakthrough of $NO_2$, and providing an indication of the remaining useful life and/or breakthrough can now be presented in context and in greater detail. It will be understood that various embodiments can be used, modified, and/or be affiliated with systems for NO inhalation therapy that can include an initial source of gas that is NO and/or $NO_2$.

In exemplary embodiments, the remaining useful life of $NO_2$-to-NO reactor cartridge can be determined and/or provided to users by one or more meters, such as dosage meters and/or flow meters. In exemplary embodiments, meters can be integral with and/or operatively associated with a $NO_2$-to-NO reactor cartridge, and/or integrated with the gas delivery system.

In exemplary embodiments, meters can include and/or be operatively associated with one or more sensors, which in turn may be operatively associated with at least a portion of the conversion reactor. Sensor can be, but is not limited to, a flow sensor, a spectrophotometric sensor, a chemical sensor, an electrochemical sensor, a pH sensor, a moisture sensor, or a combination of one or more sensors.

Principles and embodiments of the present invention also relate to determining the activity of the consumable conversion media, the concentration of various components in the gas stream at various locations in the system, or both. Consumable conversion media components of interest can include ascorbic acid, dehydroascorbic acid, nitric acid, water, or combinations thereof. Gasses of interest can include $NO_2$, NO, and $O_2$, or combinations thereof.

In various embodiments, the useful lifetime of a reactor cartridge may be determined by a number of factors including but not limited to the overall surface area of the loose or monolithic packing material, the weight of antioxidant retained on the packing material surface, the amount of $H_2O$ available to react with the antioxidant and $NO_2$, the durability of the reactor cartridge and packing material.

Principles and embodiments of the present invention relate to methods of determining the average expected lifetime of a cartridge.

The average expected lifetime of a cartridge may be determined by experimental measurements, stoichiometric calculations, or a combination thereof.

For example, the average expected lifetime may be based on the amount of consumable conversion media available to react with incoming $NO_2$ gas. This may be calculated from the molar mass of antioxidant applied to the packing material by differential weighing before and after application of the antioxidant. In addition, the reactor cartridge may be tested with a flow of $NO_2$ gas of known concentration, since actual values may differ from the calculated values due to some of the reactants being inaccessible to the gas after packing or final assembly of a reactor cartridge.

In an embodiments, a method may comprise preparing a plurality of standard weights of consumable conversion media, calculating the stoichiometric amount of reactants present in the consumable conversion media for the measured weight, passing a $NO_2$ gas through the consumable conversion media until a predetermined concentration of $NO_2$ exits the cartridge indicating that breakthrough has occurred and the consumable conversion media has been exhausted. A ratio of the measured amount of $NO_2$ conversion determined by testing to the calculated amount of $NO_2$ conversion can be determined, and the ratio correlated with the initial differential weight measured for cartridges that are not tested to exhaustion to determine an expected amount of $NO_2$ that can be converted by the cartridge. However, such untested cartridges may be tested with $NO_2$ or $N_2$ gas(es) for other determinations.

In embodiments, the average amount of consumable conversion media available to react with incoming $NO_2$ gas for each reactor cartridge may be determined, and stored in the memory chip of the cartridges for the particular production lot.

Principles and embodiments of the present invention relate to a method of testing for NO conversion efficiency across the entire working flow range of a delivery system, for example the flow patterns of a ventilator, or maximum regulated flow intended from a compressed gas cylinder. In various embodiments, a cartridge to be tested may be installed in a gas delivery system, and exposed to various operating parameters.

In an embodiment, $NO_2$ may be injected into a reactor cartridge at a specified concentration and flow rate, and the concentrations of $NO_2$ and NO detected at the outlet of the cartridge, where the total amount of $NO_2$ injected into the cartridge is less than 0.1% of the expected amount of $NO_2$ that can be converted by the cartridge, so as not to measurably reduce the expected lifetime. The injected concentration and flow rate may be varied during the test to match flow patterns of a ventilator, so different flow waveforms simulate different types of ventilation and the conversion is tested across the entire working flow range of a delivery system. This testing can confirm that a cartridge is capable of full conversion (e.g., 99.9%) even at a maximum flow rate without breakthrough.

In embodiments the values of $NO_2$ and NO detected at the outlet of the cartridge and/or a pass rating for conversion may be stored in the tested conversion cartridge.

In embodiments, the test system may comprise a computer and interlock arrangement as described herein, such that testing may not be conducted unless the cartridge is properly installed and the memory chip is in electronic communication with the computer, and capable of storing the test values.

Principles and embodiments of the present invention relate to a method of testing for channeling and structural integrity of the consumable conversion media by introducing $N_2$ at a predetermined pressure into the cartridge inlet and measuring the differential pressure drop across the conversion media. A pressure drop greater than a threshold value would indicate that a path of lower resistance is present in the reactor cartridge being tested, for example a channel and/or crack depending on the form of consumable conversion media, and the cartridge is therefore unsafe and/or inoperable.

In embodiments the values of $NO_2$ and NO detected at the outlet of the cartridge and/or a pass rating for conversion may be stored in the tested conversion cartridge.

In exemplary embodiments, a statistical number or percentage of unreacted gas molecules (e.g., $NO_2$) that would traverse the distance without conversion to a product molecule (e.g., NO), where the number may be set at an absolute concentration such as 0.1 ppm $NO_2$, or a percentage may be set at a relative amount such as 1% of $NO_2$ entering the reactor. Additional sensor locations may be positioned at other sample points of interest, such as along the periphery of the packed material to detect channeling, buried to different depths within the consumable conversion media to detect conversion fronts, and/or at the gas inlet or gas outlet to detect gas concentration(s) before or after interaction with the consumable conversion media.

Once a cartridge has been manufactured, sealed, and tested, it may be packaged for storage, delivery, and to provide a safe and protected environment before being used.

In embodiments, the packaging may provide a closed environment that prevents or reduces the shock and impacts suffered by a cartridge, while maintaining the internal moisture content. The packaging may be air-tight around the cartridge to reduce the likelihood of gases or moisture entering or escaping the cartridge during storage and/or shipment.

In embodiments, the packaging may comprise a supply of H2O, so the cartridge remains fully hydrated over prolonged periods of storage and shipping.

In embodiments, the packaging may comprise an impact sensor that could indicate whether the structural integrity of the packaged conversion cartridge may have been compromised between manufacturing and unpacking by an end user. The impact sensor may be one of the sensors described herein to be directly affixed to a cartridge, and may be in addition to an impact sensor also affixed to the packaged conversion cartridge.

Principles and embodiments of the present invention relate to systems and methods for determining if a reactor cartridge has been subjected to inappropriate handling and/or shocks that could be transmitted through the reactor cartridge housing and affect the conversion media, as might occur in a manufacturing-warehousing setting and/or during transport and storage by a customer due to rough handling of the conversion reactor by the various actors.

In embodiments of the present invention, shocks may be detected by impact sensors comprising a visually observable tube that may be affixed to and/or operatively associated with a reactor cartridge at some point during the manufacturing process, for example before or after loading of the conversion media into the cartridge body. Such a tube may change colors when it experiences a force of predetermined magnitude, thereby indicating questionable physical integrity of the cartridge prior to actual use.

An impact sensor may be calibrated to provide a physical indication that the cartridge body, and thereby any conversion media within the cartridge body, has experienced a shock of sufficient force and/or duration to compromise the physical integrity of the reactor cartridge and/or conversion media. For example, the porous cylindrical wall coated with consumable reactants of a monolithic consumable conversion media may become cracked if subjected to a sufficient force, as determined by experiments (e.g., drop tests). Similarly, the particulate matter of a packed consumable conversion media for example may fracture and thereby suffer a reduction in volume, as well as settle sufficiently to permit channeling. For example, silica granules may have a crush strength of between about 5 and 30 pounds.

In various embodiments, an impact sensor may be a solid state detector, an electromechanical detector, an electrical or electronic detector, a micro-electro-mechanical system (MEMS) detector, or a mechanical detector. The impact detectors may be accelerometers. An electromechanical detector may be, for example, a reed switch that is activated by the movement of a ring magnet, as known in the art. A solid state detector may be a Hall Effect sensor operatively associated with a magnet, as would be known in the art. An electrical or electronic detector may be for example a piezoelectric, piezoresistive or capacitive detector, as would be known in the art. A MEMS detector may be for example a cantilevered beam device, as would be known in the art.

In various embodiments, the impact sensor may be a detector in a single plane or two or more detectors operating in a plurality of perpendicular planes.

In various embodiments, the one or more impact sensor(s) may be in communication and operatively associated with suitable analog and/or digital electronics, for example a meter, that is configured to receive and measure the analog or digital electrical signal(s) produced by the impact sensor (s).

In various embodiments, the impact sensor may be configured to determine the number of impacts and/or the severity of the impact(s) experienced by the associated reactor cartridge. The values generated by the impact sensor may be stored in a non-transient memory, for example flash memory, for later retrieval and/or analysis to determine if any particular impact was sever enough to possibly compromise the integrity and/or proper functioning of a conversion cartridge, or if multiple impact events may have caused a total amount of force sufficient to damage or compromise the integrity and/or proper functioning of a conversion cartridge.

In various embodiments, the impact sensor may be affixed and/or operatively associated with a conversion cartridge to detect if and/or when the conversion cartridge experiences an impact, for example from being dropped during manufacturing, packaging shipment, stocking, installation, usage, or any other handling. In various embodiments, an impact sensor may be affixed and/or operatively associated with the packaging container within which a conversion cartridge may be placed after manufacturing for protection during shipping and storage.

Figure 7:
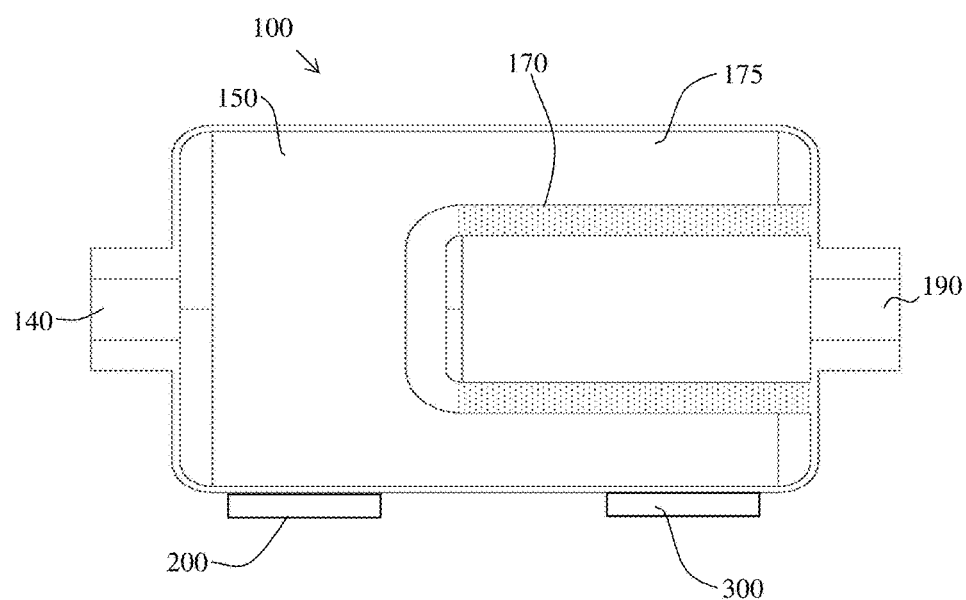
FIG. 7 illustrates an exemplary $NO_2$-NO reactor cartridge with a monolithic consumable conversion media, in accordance with exemplary embodiments of the present invention.

FIG. 7 illustrates an exemplary $NO_2$-NO reactor cartridge with a monolithic consumable conversion media, an impact sensor 200 affixed to the wall on the outside of the reactor cartridge, and a memory chip 300 affixed to the wall on the outside of the reactor cartridge, wherein the impact sensor and/or memory chip are operatively associated with the cartridge, and may be configured to be in electronic communication with a computer.

An impact sensor and/or meter may be configured to detect and/or measure the various overall accelerations and/or forces a cartridge or packaging may experience even if a sudden impact, for example from falling and hitting the ground or an object, does not occur. For example, sudden stops, starts, and turns by a truck or forklift conveying a conversion cartridge from one location to another location may generate forces on the conversion cartridge that should be monitored even though the cartridge and/or packaging appears undamaged when received by an end-user.

In various embodiments, the impact sensor may be an inertial measurement unit with multiple degrees of freedom.

In embodiments of the present invention, the determination that breakthrough of the $NO_2$ is imminent can be used to actuate a regulating device to halt the delivery of at least the $NO_2$ gas to the recipient before poisoning occurs. The regulating device may cut off flow of $NO_2$ from its source, cut off gas flow exiting the conversion reactor, divert air flow around the conversion reactor to continue air/$O_2$ delivery to a recipient without NO, or divert flow of the $NO_2$/air mixture to an auxiliary conversion reactor depending upon the system configuration and therapy protocols for the recipient.

In embodiments a sample of gas exiting the conversion reactor may be diverted from the delivery conduit into a side stream. The side stream of gases may be passed through the transparent tubular section containing the material that changes color, introduced into a spectrophotometer, a mass spectrometer (e.g. for determining the concentration of gases, etc.), or reaction vessels that produce a known chemical response to the gases of interest.

In an embodiment, one or more fiber optic probe(s) may be inserted through the annular wall of the conversion reactor, such that the probe can detect changes in the ascorbic acid, dehydroascorbic acid, nitric acid, or combinations thereof, at a location along the length of the packed reactor. A measurement of the ascorbic acid, dehydroascorbic acid, nitric acid, or combinations thereof would be indicative of the amount of consumable reactant activity remaining for the reactor, based upon the mean-free path of gaseous $NO_2$, whereby a predetermined change in ascorbic acid, dehydroascorbic acid, nitric acid, or combinations thereof indicates that the reactor has a limited conversion capacity remaining. The value of the predetermined change can be correlated with the extent of reactor life remaining or the amount of consumable conversion media used up through suitable calibration and statistical analysis.

The combination of a fiber optic sensor probe and a spectrometer a means for monitoring the functioning of the conversion reactor and determining a lifetime of the conversion media.

Principles and embodiments of the present invention relate to detecting and/or measure the presence of nitric and/or nitrous acid, and pH to determine if unconverted NO2 is reacting to form acidic by-products.

The combination of an electrochemical sensor probe and voltmeter and/or ammeter provides a means for monitoring the functioning of the conversion reactor and determining a lifetime of the conversion media.

In an embodiment, the sensor probes can be micro pH sensors that can detect changes in pH due to the conversion of ascorbic acid to dehydroascorbic acid. Micro pH sensors can have a 1 mm or sub-1 mm detection tip that can be inserted through a suitable opening in the annular wall of the conversion reactor configured and dimensioned to receive the pH sensor. The sensor can be electrically connected to an electric circuit (e.g., pH meter) that detects changes in pH, as is known in the art, and may communicate an electric signal to a computer for display and/or triggering an alarm.

The combination of a pH sensor probe and pH meter provides a means for monitoring the functioning of the conversion reactor and determining a lifetime of the conversion media.

In an embodiment, the sensor probes may be micro-conductivity sensors that can detect changes in the conductivity of the media surface due to reduced amount of water on the surface and/or differences in conductivity between the ascorbic acid and dehydroascorbic acid on the surface.

The combination of a conductivity sensor probe and voltmeter and/or ammeter provides a means for monitoring the functioning of the conversion reactor and determining a lifetime of the conversion media.

In an embodiment, the sensor probes may be magnetic probes sensors that can detect changes in the conductivity of the media surface due to reduced amount of water on the surface and/or differences in conductivity between the ascorbic acid and dehydroascorbic acid on the surface.

In an embodiment of the present invention, a meter may be placed at the distal end of the conversion reactor outlet to detect one or more gasses of interest exiting the reactor, in particular, an $NO_2$ sensor probe may be located in the delivery conduit connected to the outlet to measure the amount of $NO_2$ leaving the conversion reactor. The sensor probe may be a chemical or electrochemical sensor that reacts with the exiting $NO_2$ and converts it to another chemical species, thereby removing the detected amount of $NO_2$ from the delivery gas stream flowing to a recipient.

Principles and embodiments of the present invention relate to determining the mass and/or volumetric amount of $NO_2$ that can be converted to NO by a conversion reactor, applying a safety margin to the determined volume of $NO_2$, and recording the determined value for later reference in a memory chip affixed to the conversion cartridge.

In an embodiment, the safety factor is applied to compensate for statistical variations in manufacturing, tolerances, and performance characteristics of the reactor, as well as real-world inaccuracies in measurements. The determined value and safety factor establishes a theoretical $NO_2$ breakthrough value at which the reactor would be considered depleted and requiring replacement to maintain safe operation.

In embodiments, the amount of $NO_2$ passing into a characterized reactor cartridge can be measured by an appropriate mass flow meter(s), for example a vane flow meter, a hot wire flow meter, a membrane temperature sensor, or a Karman Vortex meter. Once the cumulative amount of $NO_2$ measured by the flow meter reaches the determined value of the reactor, flow of the $NO_2$ can be halted to prevent breakthrough to a recipient. In embodiments, a flow meter can be placed between the gas source and the conversion reactor. A valve can be placed downstream of the flow meter and before the conversion reactor. When the amount of gas passing through the flow meter reaches the theoretical $NO_2$ breakthrough value, a computer can trigger the valve downstream of the flow meter to close, thereby shutting off gas flow to the reactor and halting the delivery of $NO/NO_2$ to a recipient. In embodiments, an auxiliary air/$O_2$ line can be provided in parallel to the conversion reactor line, so that air/$O_2$ may continue to flow to the recipient after the $NO_2$ gas source is valved off.

Figure 8:
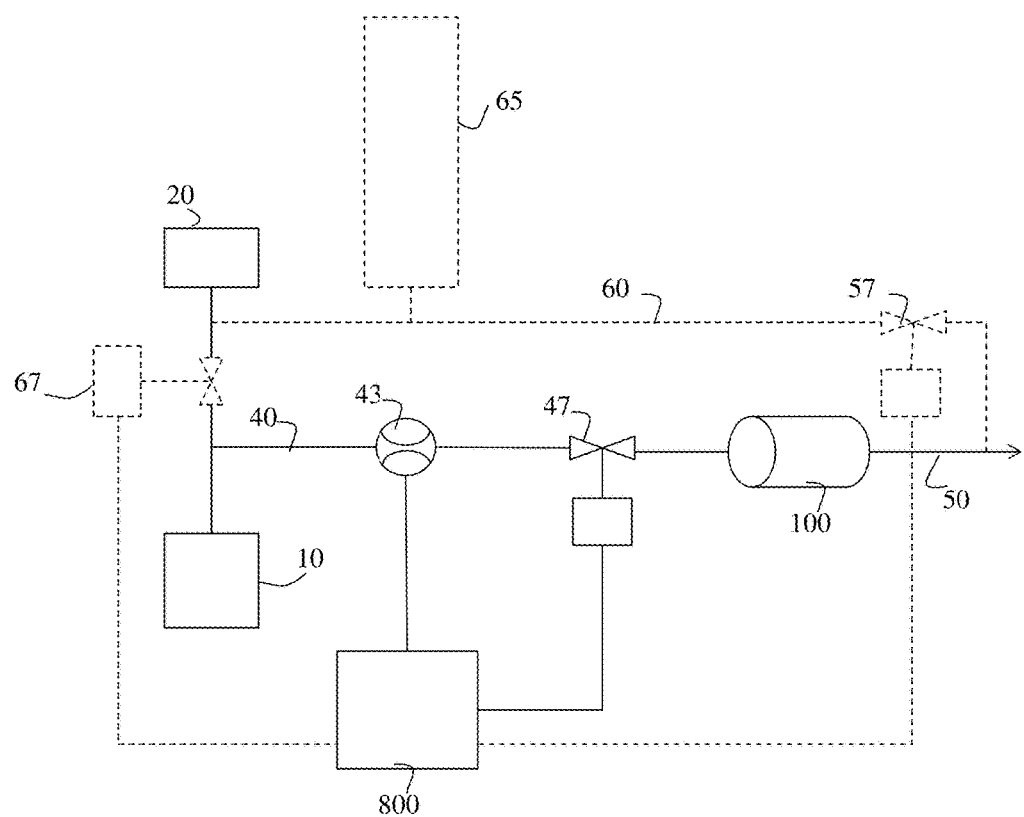
FIG. 8 illustrates an exemplary inhalation therapy system with computer controlled gas delivery, in accordance with exemplary embodiments of the present invention.

FIG. 8 illustrates a gas delivery system 1 having a gas source 10 that can supply for example $NO_2$ through a source conduit 40 to a flow meter 43. Gas exiting the flow meter can be fluidly communicated to a valve 47 and from the valve 47 to a conversion reactor 100 by the source conduit 40. Gas entering the conversion reactor 100 may be converted to a product gas, for example NO, and fluidly communicated from the reactor to a recipient through a delivery conduit 50. A computer 800 in electrical communication with the flow meter 43 monitors the amount of gas passing through the meter and can calculate the amount of $NO_2$ fed to the conversion reactor based on its concentration in the gas source 10. When the computer 800 determines that the amount of $NO_2$ fed to the conversion reactor has reached a predetermined value established for the reactor cartridge's expected life, the computer can send an electrical signal to the valve 47 triggering it to close in order to prevent toxic $NO_2$ from flowing through an exhausted conversion reactor 100 and reaching the recipient.

In an embodiment, an indication that the reactor cartridge is now exhausted may be stored in the non-transient computer readable medium in the memory chip affixed to the cartridge. This exhaustion indicator may be used to prevent the cartridge from accidently being reinstalled in a delivery system once it is no longer functional. In embodiments, the exhaustion indicator may be read by the system computer, and prevent the system from entering an operation state. An audible and/or visual warning that the cartridge is no longer any good may also be provided to a user.

In an embodiment, a valve 57 may be connected to and in fluid communication with the delivery conduit 50 and an air supply 20, and a valve 67 may be located between the air supply 20 and gas source 10. When the computer 800 determines that the amount of $NO_2$ fed to the conversion reactor has reached a predetermined value established for the reactors expected life, the computer 800 can send an electrical signal to valve 57 to open at the same time that valve 47 is triggered to close, in order to continue providing air to the recipient through the delivery conduit without any $NO_2$ or product gases. A valve 67 may be triggered to close by the computer 800 to isolate the air supply 20 from the source gas 10, so only air is provide through alternate conduit 60.

In another embodiment, a gas source 65 supplying NO may be connected to and in fluid communication with the air supply 20 and alternate conduit 60 to provide a predetermined concentration of NO to the recipient when valve 47 closes.

In embodiments of the present invention, the determination by the system computer that potential breakthrough of the $NO_2$ is imminent due to the cartridge converting the average expected amount of $NO_2$ can be used to actuate a regulating device to halt the delivery of at least the $NO_2$ gas to the recipient before poisoning occurs. The regulating device may cut off flow of $NO_2$ from its source, cut off gas flow exiting the conversion reactor, divert air flow around the conversion reactor to continue air/$O_2$ delivery to a recipient without NO, or divert flow of the $NO_2$/air mixture to an auxiliary conversion reactor depending upon the system configuration and therapy protocols for the recipient. In embodiments, when the delivery system determines the cartridge is almost expired the computer may automatically reduce the delivered NO concentration thus providing users more time to replace the cartridge. This safety feature allows delivery to continue at a reduced rate rather than shutting off completely, which could cause rebound pulmonary hypertension.

In various embodiments, a backup delivery system could provide constant flow delivery, proportional delivery to an inspiratory flow signal, or pulsatile delivery to approximate a proportional delivery system. In embodiments, the backup delivery system may be electronic or pneumatic. The backup delivery system may be designed to support manual ventilation (with an Ambu® bag). The backup delivery system may incorporate air or $O_2$ delivery for manual ventilation. In embodiments, the backup delivery system may be manually activated or electronically activated by the primary delivery system in a fail-over state. The backup delivery system may interface to the same cartridge converter systems as the primary or to a separate set. In various embodiments, the backup system cartridge converters may contain the same safety mechanisms as described for the primary delivery system in this application In various embodiments, a connector at an inlet end of the conversion cartridge and/or a connector at an outlet end of the conversion cartridge may be polarized or keyed in a manner that prevents the cartridge from being installed in a NO delivery system with an incorrect orientation (i.e., backwards). In various embodiments, different lots of manufactured conversion cartridges may be assembled with different sets of polarized or keyed connectors that prevent two cartridges from the same manufacturing batch from being installed as a redundant set of cartridges.

The flow meter and voltmeter and/or ammeter provides a means for monitoring the functioning of the conversion reactor and determining a lifetime of the conversion media.

The determined value for the characterized conversion reactor can be stored in a suitable non-volatile memory device or other non-transitory computer readable medium (e.g., 1- or 2-D bar codes) provided with or attached to the characterized reactor, or stored in the non-volatile memory of a microprocessor-based system. In an embodiment, the flow meter may be in electronic communication with the microprocessor-based system, and communicate real time measured values from a flow meter to the microprocessor-based system for determination of the remaining life of the reactor and the occurrence of a theoretical breakthrough. The breakthrough is referred to as theoretical because it is based upon the calculated value including the safety factor, so the threshold value should be reached before any actual breakthrough of $NO_2$ occurs.

Characterization of reactors can be accomplished by testing a statistical sampling of each manufactured batch of reactors to failure, averaging the volume of $NO_2$ converted to NO before reaching a breakthrough limit or consumable reactant exhaustion, and applying a suitable safety factor to adjust for both the statistical dispersion and/or variation of the measurements and variability in component and manufacturing tolerances, as well as an applicable additional safety margin to allow for example time to reach a reactor and perform the necessary replacement before actual breakthrough would occur.

It is to be understood that the present invention is not limited to the details of construction or process steps set forth in the above description. The invention is capable of other embodiments and of being practiced or being carried out in various ways.

Various exemplary embodiments of the present invention are described in more detail with reference to the figures. It should be understood that these drawings only illustrate some of the embodiments, and do not represent the full scope of the present invention for which reference should be made to the accompanying claims.

Various exemplary embodiments of the present invention can be used to deliver therapeutic gas to patients suffering from chronic obstructive pulmonary disease (COPD), idiopathic pulmonary fibrosis (IPF), and pulmonary hypertension (PH), cystic fibrosis (CF), to name a few. At times, the name of a specific disease may not be provided; however, this is merely for ease.

Although the disclosure herein has been described with reference to particular embodiments, it is to be understood that these embodiments are merely illustrative of the principles and applications of the present invention. It will be apparent to those skilled in the art that various modifications and variations can be made to the devices, systems, and methods of the present invention without departing from the spirit and scope of the present invention. Thus, it is intended that the present invention include modifications and variations that are within the scope of the appended claims and their equivalents.

Reference throughout this specification to "one embodiment," "certain embodiments," "one or more embodiments" or "an embodiment" means that a particular feature, structure, material, or characteristic described in connection with the embodiment is included in at least one embodiment of the present invention. Thus, the appearances of the phrases such as "in one or more embodiments," "in certain embodiments," "in one embodiment" or "in an embodiment" in various places throughout this specification are not necessarily referring to the same embodiment of the present invention. Furthermore, the particular features, structures, materials, or characteristics may be combined in any suitable manner in one or more embodiments.

What is claimed is:

1. A system for safely delivering a supply of NO to a recipient, comprising:
   a gas source that supplies a gas, wherein the gas comprises $NO_2$;
   a gas conduit connected to and in fluid communication with the gas source;
   a $NO_2$-to-NO reactor cartridge connected to and in fluid communication with the gas conduit, so as to allow gas to flow from the gas source to an inlet end of the reactor cartridge, wherein the reactor cartridge facilitates conversion of the $NO_2$ gas delivered to the inlet end to an outgoing NO gas exiting at an outlet end of the reactor cartridge;
   a flow meter connected to and in fluid communication with the inlet end of the reactor cartridge and gas conduit to monitor the amount of $NO_2$ gas delivered to the reactor cartridge;
   a delivery conduit connected to and in fluid communication with the outlet end of the reactor cartridge that allows NO gas from the reactor cartridge to flow to a recipient;
   a valve connected to and in fluid communication with the delivery conduit to close off the flow of gas to the recipient; and
   a computer in electronic communication with the flow meter over a flow meter communication path, and in electronic communication with the valve, wherein the computer is configured to receive electronic signals from the flow meter and calculate a usage value for comparison with a predetermined threshold value, and configured to generate an actuating signal when the usage value reaches the threshold value, and communicate the actuating signal to the valve to close and stop the flow of gas to the recipient.

2. The system of claim 1, which further comprises an outer housing encasing the gas source, wherein the outer housing is large enough to encapsulate the gas source and form an internal volume between the inside of the outer housing and the gas source.

3. The system of claim 2, which further comprises an absorbent material held within the internal volume which is sufficient to react with all of the material potentially released from the gas source.

4. The system of claim 3, which further comprises color agents intermixed with the absorbents, so that a color change of the color agent occurs when the absorbent interacts with the $NO_2$.

5. The system of claim 1, which further comprises an $NO_2$ sensor operationally associated with the delivery conduit to determine the presence of an unacceptable level of $NO_2$ in the gas being directed to the recipient.

6. The system of claim 1, which further comprises an impact sensor operationally associated with the reactor cartridge to determine the level of shocks sustained by the reactor cartridge.

7. The system of claim 1, which further comprises a memory chip operationally associated with the reactor cartridge to store reactor cartridge data on a non-transient computer readable medium, and wherein the memory chip is configured to be in electronic communication with the computer.

8. The system of claim 7, wherein the computer is configured to be in electronic communication with the memory chip over a memory chip communication path, and can read the reactor cartridge data stored on a non-transient computer readable medium; and
   wherein the computer is configured to communicate the actuating signal to the valve to close and stop the flow of gas to the recipient if the reactor cartridge data indicates the reactor cartridge is inoperable.

9. The system of claim 8, which further comprises a cartridge installation detector in electronic communication with the computer over a detector communication path that identifies when the reactor cartridge is properly coupled to the gas conduit and delivery conduit, and sends the actuating signal to the computer when the proper coupling of the reactor cartridge is detected; and
   wherein the computer prevents the gas delivery system from entering an operational state until the actuating signal is received from the cartridge installation detector.

10. The system of claim 9, wherein the computer is configured to receive electronic signals from the flow meter and calculate a usage value, and store the calculated usage value on the non-transient computer readable medium of the microchip for later reference, and
   wherein the computer prevents the gas delivery system from entering an operational state if the calculated usage data stored on the non-transient computer readable medium equals or exceeds the stored average expected lifetime of the reactor cartridge.

* * * * *